US008632612B2

(12) United States Patent
Yontz

(10) Patent No.: US 8,632,612 B2
(45) Date of Patent: Jan. 21, 2014

(54) COMPOSITIONS FOR DYEING KERATIN FIBERS

(75) Inventor: Dorie J. Yontz, Bloomington, MN (US)

(73) Assignee: Segetis, Inc., Golden Valley, MN (US)

( * ) Notice: Subject to any disclaimer, the term of this patent is extended or adjusted under 35 U.S.C. 154(b) by 0 days.

(21) Appl. No.: 13/818,317

(22) PCT Filed: Sep. 7, 2011

(86) PCT No.: PCT/US2011/050651
§ 371 (c)(1),
(2), (4) Date: Mar. 1, 2013

(87) PCT Pub. No.: WO2012/033813
PCT Pub. Date: Mar. 15, 2012

(65) Prior Publication Data
US 2013/0156716 A1   Jun. 20, 2013

Related U.S. Application Data

(60) Provisional application No. 61/380,518, filed on Sep. 7, 2010.

(51) Int. Cl.
*A61Q 5/10* (2006.01)
*C07D 317/00* (2006.01)

(52) U.S. Cl.
USPC ............. 8/405; 8/435; 8/572; 8/576; 549/448

(58) Field of Classification Search
USPC ........................ 8/405, 435, 572, 576; 549/448
See application file for complete search history.

(56) References Cited

U.S. PATENT DOCUMENTS

| | | | |
|---|---|---|---|
| 1,934,309 A | 11/1933 | Hoover | |
| 2,008,720 A | 7/1935 | Lawson | |
| 2,260,261 A | 10/1941 | Morey et al. | |
| 2,556,135 A | 6/1951 | Croxall et al. | |
| 2,985,536 A | 5/1961 | Stein et al. | |
| 3,201,420 A | 8/1965 | Fuzesi et al. | |
| 3,855,248 A | 12/1974 | Lannert et al. | |
| 4,460,767 A | 7/1984 | Matsumura et al. | |
| 4,465,866 A | 8/1984 | Takaishi et al. | |
| 4,737,426 A | 4/1988 | Roth | |
| 4,792,411 A | 12/1988 | Walsh | |
| 4,806,448 A | 2/1989 | Roth | |
| 5,013,543 A | 5/1991 | Mercado et al. | |
| 5,093,111 A | 3/1992 | Baker et al. | |
| 5,266,592 A | 11/1993 | Grub et al. | |
| 5,289,384 A | 2/1994 | Akiyama | |
| 5,516,459 A | 5/1996 | Van Eenam | |

(Continued)

FOREIGN PATENT DOCUMENTS

| | | | |
|---|---|---|---|
| CA | 1000285 | | 11/1976 |
| CA | 2347255 A1 | | 2/2004 |
| DE | 3220035 A1 | | 1/1983 |
| DE | 10036423 A1 | | 3/2001 |
| EP | 012543 A1 | | 6/1980 |
| EP | 0308956 A2 | | 3/1989 |
| EP | 0507190 A1 | | 10/1992 |
| EP | 0913463 A1 | | 5/1999 |
| FR | 1445013 | | 7/1966 |
| JP | 2800437 A | | 9/1953 |
| JP | 4217972 | | 8/1992 |
| JP | 2004075586 | | 3/2004 |
| JP | 2006143702 A | | 6/2006 |
| SU | 722912 | | 3/1980 |
| WO | 9412489 A1 | | 6/1994 |
| WO | 2004099173 A1 | | 11/2004 |
| WO | 2007062118 A2 | | 5/2007 |
| WO | W02008046795 A1 | | 10/2007 |
| WO | 2008089463 A2 | | 7/2008 |
| WO | 2008098375 A1 | | 8/2008 |
| WO | 2009032905 A1 | | 3/2009 |

OTHER PUBLICATIONS

STIC Search Report dated Jul. 5, 2013.*
Holmberg, Krister, "Surfactants with controlled half-lives", Current Opinion in Colloid & Interface Science, vol. 1, Issue 5, pp. 572-579 (Oct. 1996).
Transmittal and International Preliminary Report on Patentability for PCT/US2011/050651 mailed Mar. 21, 2013, 9 pages.
Brigl, Percy, et al., "The Reaction of the Pyruvic Acid with Glycerin," Annalen der Chemie 476: p. 215-232, (with English translation).
Calinaud, et al., "Cyclic acetal series. XIII. Opening of 4-oxo and 4-hydroxy-3,6,8-trioxabicyclo[3.2.1]octane and 3-pxp-2,5,7-trioxabicyclo[2.2.2]octane rings by lithium aluminum hydride and methylmagnesium iodide," Carbohydrate Research 30(1) 35-43 (1973).
Carey, et al., "Advanced Organic Chemistry, Second Edition, Part B: Reactions and Synthesis," Plenum Press 539-552 (1983).
Cuiling, et al., "Synthesis of Levulinic Ketals with Furfuryl Alcohol as Raw Material," Journal of Huagiao University (Nature Science) 23(3): 257-259 (2002) (English Translation).
Horsfall, et al., "Fungitoxicity of Dioxanes, Dioxolanes, and Methylenedioxybenzenes," The Connecticut Agricultrual Experiment Station New Haven, Bulletin 673: 1-44, Jun. 1965.
Transmittal and International Search Report for PCT/US2011/050651, mailed Apr. 26, 2012, 6 pages.
Meltzer, et al., "2,2-Disubstituted 1,3-Dioxolanes and 2,2-Disubstituted 1,3-Dioxanes," JOC 25: 712-715 (1960).
Meskens, Frans A.J., "Methods for the Preparation of Acetals from Alcohols or Oxiranes and Carbonyl Compounds," Synthesis 501-522 (1981).
Nakamura, et al., "Study on Ketalization Reaction of Poly (vinyl alcohol) by Ketones. IX. Kinetic Study on Acetalization and Ketalization Reaction of 1,3-Butanediol as a Model Compound for Poly (vinyl alcohol)," Polymer Science Part B: Polymer Physics 35(9): 1719-1731 (2000).
Newman, et al.,"Kinetic and Equilibrium Studies of Cyclic Ketal Formation and Hydrolysis," The Journal of the American Oil Chemists Society 80: 6350-6355 (1958).
Olson, Edwin S., "Subtask 4.1—Conversion of Lignocellulosic Material to Chemicals and Fuels," Final Report for U.S. Dept. of Energy, National Energy Technology Laboratory, Cooperative Agreement No. DE-FC26-98FT40320 (Jun. 2001).
Written Opinion of the International Searching Authority for PCT/US2011/050651, mailed Apr. 26, 2012, 7 pages.

*Primary Examiner* — Eisa Elhilo
(74) *Attorney, Agent, or Firm* — Cantor Colburn LLP

(57) ABSTRACT

Disclosed herein are compositions for dyeing keratin fibers, methods of manufacture thereof and articles comprising the same.

22 Claims, No Drawings

(56) References Cited

U.S. PATENT DOCUMENTS

| | | |
|---|---|---|
| 5,705,087 A | 1/1998 | Mushrush et al. |
| 5,859,263 A | 1/1999 | Ghorpade et al. |
| 5,917,059 A | 6/1999 | Bruchmann et al. |
| 5,998,092 A | 12/1999 | McCulloch et al. |
| 6,010,995 A | 1/2000 | Van Eenam |
| 6,034,118 A | 3/2000 | Bischofberger et al. |
| 6,036,925 A | 3/2000 | Adams et al. |
| 6,306,249 B1 | 10/2001 | Galante et al. |
| 6,528,025 B1 | 3/2003 | Boesch et al. |
| 6,627,181 B1 | 9/2003 | Busch, Jr. et al. |
| 6,806,392 B2 | 10/2004 | Boesch et al. |
| 7,094,395 B1 | 8/2006 | Qu et al. |
| 2003/0036489 A1 | 2/2003 | Liu et al. |
| 2003/0167681 A1 | 9/2003 | Delgado Puche |
| 2004/0024260 A1 | 2/2004 | Winkler et al. |
| 2004/0138090 A1 | 7/2004 | Drapier et al. |
| 2004/0157759 A1 | 8/2004 | Scherubel |
| 2004/0167245 A1 | 8/2004 | Chappelow et al. |
| 2005/0233927 A1 | 10/2005 | Scherubel |
| 2006/0207037 A1* | 9/2006 | Fadel et al. ............. 8/406 |
| 2007/0111917 A1 | 5/2007 | Lang et al. |
| 2008/0081779 A1 | 4/2008 | Holscher |
| 2008/0124426 A1 | 5/2008 | Kobler et al. |
| 2008/0242721 A1 | 10/2008 | Selifonov |
| 2008/0305978 A1 | 12/2008 | Wietfeldt et al. |
| 2010/0087357 A1 | 4/2010 | Morgan, III et al. |
| 2011/0196081 A1 | 8/2011 | Kwon et al. |
| 2011/0300083 A1 | 12/2011 | Yontz et al. |

* cited by examiner

COMPOSITIONS FOR DYEING KERATIN FIBERS

CROSS-REFERENCE TO RELATED APPLICATIONS

This application is a national stage application of PCT/US2011/050651, filed Sep. 7, 2011, which claims priority to U.S. provisional application 61/380,518 filed Sep. 7, 2010, both of which are hereby incorporated by reference in their entirety.

BACKGROUND

The present invention generally relates to compositions for dyeing keratin fibers. More specifically, the present invention is directed to compositions for dyeing keratin fibers, such as hair, which employ alkyl ketal esters as solvents or co-solvents.

A large number of formulated products for dyeing hair are produced and sold. Because these products differ enormously, as do the conditions under which they are used, the individual products tend to be formulated specifically for the end-use application for which they are intended.

Formulators of products for dyeing keratin fibers, such as hair dyeing products, often find themselves simultaneously addressing many product needs which are often competing and sometimes even contradictory. For example, many hair dyeing formulations contain an active (such as a hair dye), which lends particular functional attributes to the product. In many cases, it is desirable to increase the concentration of the active, or to produce a product that contains the active in a specific type of product form (such as a solution, lotion, cream, gel, etc.), but the formulator is limited by the solubility of the active in the other ingredients in the product. There are several approaches to dealing with this problem, including the use of various types of emulsifiers, oils, cosolvents, and the like, but it is quite often the case that other requirements, such as the form of the product, are incompatible with the presence of such materials in large quantities. These product form concerns may be imposed by the way in which the particular product is to be applied and used; in other cases, these may be due to consumer preferences and/or expectations. Sometimes both factors are at play.

In other cases, the presence or absence of specific materials is important. In this regard there is a desire to reduce or even eliminate the presence of volatile organic compounds from hair dyeing formulations, in favor of alternative solvents. Some formulatory ingredients, such as ethanol, can dry the skin and in some cases are to be avoided for that reason, or for other reasons, such as VOC regulations in some jurisdictions or flammability concerns. Conversely, there are other cases in which ethanol and/or another relatively volatile material is wanted, so the product dries rapidly when it is applied, for example. Nonetheless, it remains necessary to include the active, and it is often desirable to provide the active in a high concentration.

In many cases, the addition of emulsifiers, oils, cosolvents and like materials can cause the product to spread poorly, or feel greasy or heavy. This concern exists even in general purpose products that contain no actives, but concerns exist in active-containing products as well. It would be desirable in some cases to provide hair dyeing compositions which have good spreading characteristics, a non-greasy feel and/or a less heavy feel. Moreover, the use of materials based on renewable resources is becoming of increasing interest as formulators redesign their products to meet environmental sensitivities of their consumer bases.

Yet, another consideration is the compatibility amongst the various ingredients, because many hair dyeing formulations contain both hydrophilic and hydrophobic components. These ingredients tend not to mix into each other. In order to create a product which does not rapidly separate into oil-rich and water-rich layers, it is often necessary to include a number of emulsifiers, cosolvents, or thickeners into the product, so it becomes kinematically stable. These emulsifiers, cosolvents, and thickeners often play little role in the function or performance of the product (i.e., are not "actives"), although they can affect the spreading characteristics and feel on the skin and in the hair. They mainly are present to permit the various functional ingredients to coexist in a stable product form or to provide a desired feel or consistency to the product. The need to include these can lead to a lot of complexity in the formulations, and/or the inclusion of ingredients (such as volatile or drying organic solvents, for example) which would more preferably be omitted. In addition, the formulations tend to be very sensitive to small compositional changes. Small changes to a formulation often destabilize it, requiring a new balance of ingredients.

SUMMARY

There is a need for simplified kersatin fiber dyeing formulations, such as hair dyeing formulations, which nonetheless provide the needed product attributes and functions. In other cases, there is a need to reduce the quantities of the various formulary components in order to reduce costs and simplify formulating. Yet, in some cases, there is a need to increase the solubility of the active in order to produce a concentrate. It is to solving these needs the present invention is directed.

In one aspect, the invention is directed to a composition for dyeing keratin fibers, such as a hair dyeing composition, comprising at least one colorant, at least one solvent and a ketal adduct of formula (I):

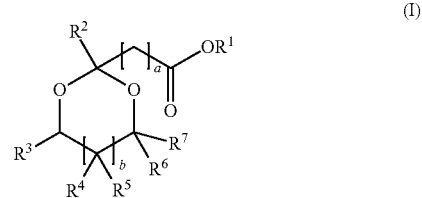

wherein
$R^1$ is $C_{1-6}$ alkyl,
$R^2$ is hydrogen or $C_{1-3}$ alkyl,
each $R^3$, $R^4$, and $R^5$ is independently hydrogen or $C_{1-6}$ alkyl,
$R^6$ is hydrogen or $C_{1-6}$ alkyl, or hydroxymethyl, specifically hydrogen or a $C_{1-6}$ alkyl,
$R^7$ is hydrogen, $C_{1-6}$ alkyl, $C_{1-6}$ alkyl substituted with up to four $OR^8$ groups wherein $R^8$ is hydrogen, $C_{1-6}$ alkyl, or acetyl, specifically hydrogen, $C_{1-6}$ alkyl, $C_{1-6}$ alkyl substituted with one hydroxy group, or $C_{1-6}$ alkyl substituted with up to three $OR^8$ groups wherein $R^8$ is a $C_{1-6}$ alkyl group or an acetyl group,
a is 0-3, and
b is 0-1.

In another aspect of the present invention, the hair dyeing composition comprises at least one colorant and a ketal adduct of formula (1).

The composition of the present invention can further contain one or more of the following components: at least one oxidizing agent, at least one carbonate ion source, at least one alkalizing agent, at least one pH buffer, at least one radical scavenger, at least one surfactant, at least one gel network thickener, at least one polymer, at least one conditioning agent, at least one chelant, at least one auxiliary agent or any combination thereof. The at least one auxiliary agent includes an amino acid, a protein, a cationic conditioner, a cationic polymer, a wax, an antioxidant, a vitamin, an alpha hydroxy acid, a beta hydroxy acid, an alpha ketoacid, an antibacterial agent, a preservative, a perfume, a sequestering agent, an anti-dandruff agent, skin protecterants, hair relaxers, and mixtures thereof.

DETAILED DESCRIPTION

The inventors hereof have discovered that the ketal adducts of ketocarboxy esters, in particular levulinate esters, offer a combination of properties that are useful for dyeing keratin fibers, such as hair dyeing compositions. The broad solubilities of the ketal adducts renders them useful in a broad variety of compositional types, including aqueous and organic compositions. The ketal adducts are particularly useful in mixed aqueous-organic systems. A further advantage is that certain of the ketal adducts, such as the levulinate ester ketals, can be derived from biological feedstocks.

The ketocarboxy ester ketals, which are sometimes referred to herein as "ketal adducts" have the general formula (I):

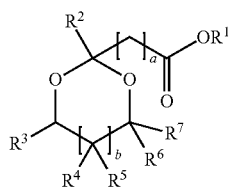

(I)

wherein $R^1$ is $C_{1-6}$ straight chain or branched alkyl, $R^2$ is hydrogen or $C_{1-3}$ alkyl, $R^3$ is hydrogen, $C_{1-6}$ straight chain or branched alkyl, $C_{1-6}$ alkyl substituted with up to four $OR^8$ groups wherein $R^8$ is hydrogen, $C_{1-6}$ alkyl, or acetyl, $R^4$ and $R^5$ are independently hydrogen or $C_{1-6}$ straight chain or branched alkyl, $R^6$ is hydrogen or $C_{1-6}$ alkyl, or hydroxymethyl, specifically hydrogen or a $C_{1-6}$ alkyl, $R^7$ is hydrogen, $C_{1-6}$ alkyl, $C_{1-6}$ alkyl substituted with up to four $OR^8$ groups, specifically hydrogen, $C_{1-6}$ alkyl, $C_{1-6}$ alkyl substituted with one hydroxy group, or $C_{1-6}$ alkyl substituted with up to three $OR^8$ groups wherein $R^8$ is a $C_{1-6}$ alkyl group or an acetyl group, a is 0-3, and b is 0-1.

More specifically, $R^1$ is $C_{1-6}$ alkyl, $R^2$ is methyl, each $R^3$, $R^4$, and $R^5$ is independently hydrogen or $C_{1-3}$ alkyl, $R^6$ is hydrogen, $C_{1-3}$ alkyl, or hydroxymethyl, $R^7$ is hydrogen, $C_{1-3}$ alkyl, or $C_{1-4}$ alkyl substituted with up to four —$OR^8$ groups, wherein $R^8$ is hydrogen or a $C_{1-3}$ alkyl group, a is 1-3, and b is 0-1.

Even more specifically $R^1$ is $C_{1-4}$ alkyl, $R^2$ is methyl, $R^3$ is hydrogen, $R^6$ is hydrogen, $C_{1-3}$ alkyl, or hydroxymethyl, $R^7$ is hydrogen, $C_{1-3}$ alkyl, or $C_{1-4}$ alkyl substituted with up to four —OR groups wherein $R^8$ is hydrogen or a $C_{1-3}$ alkyl group, a is 2-3, and b is 0.

In a specific embodiment $R^1$ is $C_{1-4}$ alkyl or acetyl, $R^2$ is methyl, $R^3$ is hydrogen, $R^6$ is hydrogen, methyl, ethyl, or —$CH_2OH$, $R^7$ is methyl, ethyl, —$CH_2OH$, —$CH_2OCH_3$, —$CH_2OCH_2CH_3$, —$CH(OH)CH_2OH$, or —$(CH(OH))_3CH_2OH$, a is 2, and b is 0.

Still more specifically, the ketal adduct of formula (1) is the glycol adduct of a levulinic acid ester having formula (1a), or the 1,2-propanediol adduct of a levulinic acid ester, having formula (1b):

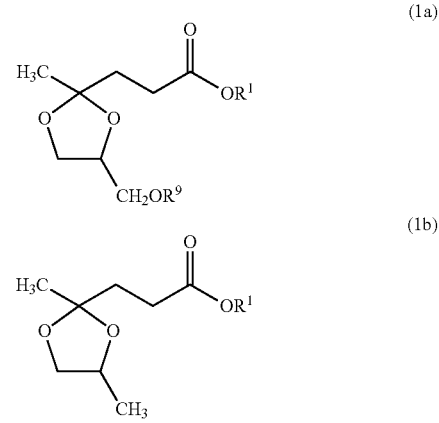

wherein $R^1$ is as defined above, specifically a $C_{1-4}$ alkyl, more specifically ethyl or butyl, and $R^9$ is hydrogen or $C_{1-4}$ alkyl. Ethyl levulinate glycerol ketal ("EtLGK") is obtained when $R^1$ is ethyl and $R^9$ is hydrogen in formula (1a), and ethyl levulinate propylene glycol ketal ("EtLPK") is obtained when $R^1$ is ethyl in formula (1b).

The ketal adducts of formula (1) can be obtained by the acid-catalyzed reaction of the corresponding ketoacid ester of formula (2) with a polyol of formula (3):

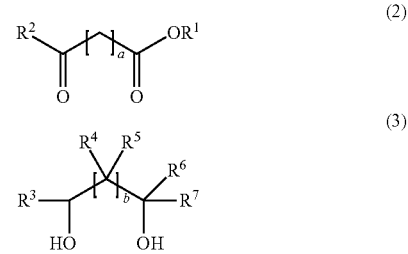

wherein each of $R^1$, $R^2$, $R^3$, $R^4$, $R^6$, and $R^7$, and a and b are as defined above. Reaction conditions are described in WO 09/032,905, for example. Many of the compounds falling within the scope of formulas (2) and (3) can be bio-sourced. The ketal adducts thus provide an entry point for a broad variety of bio-sourced solvents. For example, levulinic acid is produced by the thermochemical treatment of various carbohydrates such as cellulose; subsequent esterification with bio-sourced alkanols and ketalization of the levulinate ester with polyhydroxy compounds such glycerol or propylene glycol produces a bioderived solvent.

In a highly advantageous feature, selection of each of the specific $R^1$, $R^2$, $R^3$, $R^4$, $R^6$, and $R^7$ groups and a and b in the ketal adducts of formula (1) allows the chemical and physical properties of the ketal adducts to be adjusted to achieve the desired combination of properties, for example, solubilizing activity, coupling solvent activity, surface tension reduction, and volatility. The ability to adjust each of these features using a single scaffold provides greater flexibility in designing solvents that achieve the technical requirements of the foregoing compositions.

Thus, in a specific embodiment each of the specific $R^1$, $R^2$, $R^3$, $R^4$, $R^6$, and $R^7$ groups and a and b are selected to provide a desired solubilizing activity, that is, the ability of the ketal adduct to solubilize a solute. The presence of ester, ether-like, and optionally hydroxyl functionality allows interaction of the ketal adduct with a variety of solute functional groups.

In addition to solubilization, the ketal adducts (1), specifically (1a) and (1b) can effective coupling solvents. Coupling solvents act to solubilize two components that are wholly or partially immiscible in the absence of the coupling solvent, for example, mixtures of oil and water. Effective coupling solvents generally have both lipophilic and hydrophilic character. Appropriate selection of each of the specific $R^1$, $R^2$, $R^3$, $R^4$, $R^6$, and $R^7$ groups and a and b can provide effective coupling agents for a variety of immiscible systems. EtLGK in particular demonstrates coupling ability in aqueous systems.

The ketal adducts (1), specifically (1a) and (1b) can further be used to reduce the surface tension of solvents such as water. The surface tension of water is 72 dynes/cm at 25° C., which means that it would take a force of 72 dynes to break a surface film of water 1 cm long. The surface tension of water is quite high among common liquids and arises from the polar nature of the water molecule. For a liquid to wet the surface of a solid, the surface tension of the liquid must be lower than the solid surface tension. So, while water is generally a preferred carrier because of its low cost and low flammability, its surface tension must be reduced in many applications so it can spread and wet surfaces. Appropriate selection of each of the specific $R^1$, $R^2$, $R^3$, $R^4$, $R^6$, K and $R^7$ groups and a and b can provide effective agents to reduce surface tension in a variety of aqueous systems. EtLGK in particular demonstrates the ability to effectively reduce surface tension of aqueous solutions without the environmental and VOC issues affiliated with other solvents.

The ketal adducts (1), specifically (1a) and (1b) are further advantageous due to their low volatility. Volatility manifests itself in a number of key properties for solvents, including boiling point, vapor pressure, relative evaporation rate, flammability, odor, and volatile organic compound (VOC) content. The desired volatility profile of a solvent varies considerably by application, and there are often conflicting considerations. For instance, highly volatile process solvents require less energy to remove after use, but in many cases also require special handling due to higher flammability. Appropriate selection of each of the specific $R^1$, $R^2$, $R^3$, $R^4$, $R^6$, K and $R^7$ groups and a and b can further provide a selected volatility. EtLGK and EtLPK in particular are of acceptably low volatility and low flammability.

As stated above, the ketal adducts (1), for example, (1a) and (1b), are useful in compositions for dyeing keratin fibers. More specifically, such ketal adducts are useful in hair dyeing compositions. Furthermore, EtLGK and EtLPK are useful in compositions for dyeing keratin fibers, such as hair dyeing compositions. The ketal adducts have excellent combination of properties for use in this application, including solubilizing activity, coupling activity, low flammability, biodegradation, non-corrosiveness, and low odor.

The ketal adducts can be present in the hair dying compositions in an amount up to 50% by weight of the amount of solvent present in the composition. Alternatively, the ketal adduct can replace the solvent entirely. Accordingly, when a solvent is not present in the composition, the ketal adduct is present in an amount from about 10% by weight to about 95% by weight, typically in an amount from about 40% by weight to about 90% by weight and more typically from about 60% by weight to 80% by weight, based on the weight of the composition as a whole.

Typically, the solvent in the composition is present in an amount from about 10% by weight to about 95% by weight, typically in an amount from about 40% by weight to about 90% by weight and more typically from about 60% by weight to 80% by weight, based on the weight of the composition as a whole.

The composition of the present invention can further contain one or more of the following components: at least one oxidizing agent, at least one carbonate ion source, at least one alkalizing agent, at least one pH buffer, at least one radical scavenger, at least one surfactant, at least one gel network thickener, at least one polymer, at least one conditioning agent, at least one chelant, at least one auxiliary agent or any combination thereof. The at least one auxiliary agent includes an amino acid, a protein, a cationic conditioner, a cationic polymer, a wax, an antioxidant, a vitamin, an alpha hydroxy acid, a beta hydroxy acid, an alpha ketoacid, an antibacterial agent, a preservative, a perfume, a sequestering agent, an anti-dandruff agent, skin protectant, botanical extract, and mixtures thereof.

Colorants

Keratin fiber dyeing compositions as disclosed herein, for example hair dyeing compositions, comprise colorants, which include, but are not limited to, oxidative hair dye precursors (known as developers or primary intermediates) that deliver a variety of hair colors to the hair. Such precursors are activated by the oxidizing agent and react with further molecules to form a larger colored complex in the hair shaft. The precursors can be used alone or in combination with other precursors, and one or more can be used in combination with one or more couplers. Couplers (also known as color modifiers or secondary intermediates) are generally colorless molecules that form colors in the presence of activated precursors, and are used with other precursors or couplers to generate specific color effects or to stabilize the color.

One or more oxidative dye precursors can be present in the dyeing composition in an amount between 0.0005% to 25% by weight, based on the weight of the composition as a whole. In another aspect such oxidative dye precursors can be present in the dyeing composition in an amount between 0.005% to 20% by weight, based on the weight of the composition as a whole. Yet, in another aspect such oxidative dye precursors can be present in the dyeing composition in an amount between 0.05% to 15% by weight, based on the weight of the composition as a whole. Still, in another aspect such oxidative dye precursors can be present in the dyeing composition in an amount between 0.05% to 10% by weight, based on the weight of the composition as a whole. Additionally, the dying composition can have one or more oxidative die precursors present in an amount of 0.0005, 0.005, 0.05, 1, 2, 3, 4, 5, 6, 7, 8, 9, 10, 11, 12, 13, 14, 15, 16, 17, 18, 19, 20, 21, 22, 23, 24, 25% or any range between any of these numbers, by weight, based on the weight of the composition as a whole.

Couplers can be present in the dyeing composition in an amount between 0.0001% to 25% by weight, based on the weight of the composition as a whole. In another aspect couplers can be present in the dyeing composition in an amount between 0.0001% to 20% by weight, based on the weight of the composition as a whole. Yet, in another aspect couplers can be present in the dyeing composition in an amount between 0.001% to 10% by weight, based on the weight of the composition as a whole. Still, in another aspect couplers can be present in the dyeing composition in an amount between 0.05% to 8% by weight, based on the weight of the composition as a whole. Additionally, the dying composition can have couplers present in an amount of 0.0001, 0.001, 0.05, 1, 2, 3, 4, 5, 6, 7, 8, 9, 10, 11, 12, 13, 14, 15, 16, 17, 18, 19, 20, 21, 22, 23, 24, 25% or any range between any of these numbers, by weight, based on the weight of the composition as a whole.

The choice of precursors and couplers is determined by the color, shade and intensity of coloration that is desired. Precursors and couplers can be used herein, singly or in combination, to provide dyes having a variety of shades ranging from ash blonde to black.

These compounds are well known in the art, and include aromatic diamines, aromatic diols, aminophenols, and their derivatives (a representative but not exhaustive list of oxidation dye precursor can be found in Sagarin, "Cosmetic Science and Technology", Interscience, Special Edn. Vol. 2 pages 308 to 310). The precursors detailed below are exemplary and not intended to limit the compositions and processes disclosed herein.

Suitable couplers for use in the hair dyeing compositions of the present invention include, but are not limited to, phenols, resorcinol and naphthol derivatives. Examples of coupler substances include, but are not limited to, naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, 7-amino-4-hydroxy-naphthalene-2-sulfonic acid, 2-isopropyl-5-methylphenol, 1,2,3,4-tetrahydro-naphthalene-1,5-diol, 2-chloro-benzene-1,3-diol, 4-hydroxy-naphthalene-1-sulfonic acid, benzene-1,2,3-triol, naphthalene-2,3-diol, 5-dichloro-2-methylbenzene-1,3-diol, 4,6-dichlorobenzene-1,3-diol, 2,3-dihydroxy-[1,4]naphthoquinone; and 1-Acetoxy-2-methylnaphthalene; m-phenylenediamines such as: 2,4-diaminophenol, benzene-1,3-diamine, 2-(2,4-diamino-phenoxy)-ethanol, 2-[(3-amino-phenyl)-(2-hydroxy-ethyl)-amino]-ethanol, 2-methyl-benzene-1,3-diamine, 2-[[2-(2,4-diamino-phenoxy)-ethyl]-(2-hydroxy-ethyl)-amino]-ethanol, 4-{3-[(2,4-diaminophenyl)oxy]-propoxy}benzene-1,3-diamine, 2-(2,4-diamino-phenyl)-ethanol, 2-(3-amino-4-methoxy-phenylamino)-ethanol, 4-(2-amino-ethoxy)-benzene-1,3-diamine, (2,4-diamino-phenoxy)-acetic acid, 2-[2,4-diamino-5-(2-hydroxy-ethoxy)-phenoxy]-ethanol, 4-ethoxy-6-methyl-benzene-1,3-diamine, 2-(2,4-diamino-5-methyl-phenoxy)-ethanol, 4,6-dimethoxy-benzene-1,3-diamine, 2-[3-(2-hydroxy-ethylamino)-2-methyl-phenylamino]-ethanol, 3-(2,4-diamino-phenoxy)-propan-1-ol, N-[3-(dimethylamino)phenyl]urea, 4-methoxy-6-methylbenzene-1,3-diamine, 4-fluoro-6-methylbenzene-1,3-diamine, 2-({3-[(2-hydroxyethyl)amino]-4,6-dimethoxyphenyl}-amino)ethanol, 3-(2,4-diaminophenoxy)-propane-1,2-diol, 2-[2-amino-4-(methylamino)-phenoxy]ethanol, 2-[(5-amino-2-ethoxy-phenyl)-(2-hydroxy-ethyl)-amino]-ethanol, 2-[(3-aminophenyl)amino]ethanol, 2,4-Diamino-5-(2'-hydroxyethyloxy)toluene; N,N-Dimethyl-3-ureidoaniline; N-(2-aminoethyl)benzene-1,3-diamine, 4-{[(2,4-diaminophenyl)oxy]methoxy}-benzene-1,3-diamine, 1-methyl-2,6-bis(2-hydroxyethylamino)benzene; and 2,4-dimethoxy-benzene-1,3-diamine; m-aminophenols such as: 3-aminophenol, 2-(3-hydroxy-4-methyl-phenylamino)-acetamide, 2-(3-hydroxy-phenylamino)-acetamide, 5-amino-2-methyl-phenol, 5-(2-hydroxyethylamino)-2-methyl-phenol, 5-amino-2,4-dichloro-phenol, 3-amino-2-methyl-phenol, 3-amino-2-chloro-6-methyl-phenol, 5-amino-2-(2-hydroxy-ethoxy)-phenol, 2-chloro-5-(2,2,2-trifluoro-ethylamino)-phenol, 5-amino-4-chloro-2-methyl-phenol, 3-cyclopentylamino-phenol, 5-[(2-hydroxyethyl)amino]-4-methoxy-2-methylphenol, 5-amino-4-methoxy-2-methylphenol, 3-(dimethylamino)phenol, 3-(diethylamino)phenol, 5-amino-4-fluoro-2-methylphenol, 5-amino-4-ethoxy-2-methylphenol, 3-amino-2,4-dichloro-phenol, 3-[(2-methoxyethyl)amino]phenol, 3-[(2-hydroxyethyl)amino]phenol, 5-amino-2-ethyl-phenol, 5-amino-2-methoxyphenol, 5-[(3-hydroxy-propyl)amino]-2-methylphenol, 3-[(3-hydroxy-2-methylphenyl)-amino]propane-1,2-diol, 3-[(2-hydroxyethyl)amino]-2-methyl phenol; 1-Methyl-2-hydroxy-4-(2'-hydroxyethyl)amino-benzene; 1,3-Bis-(2,4-Diaminophenoxy)propane; 1-Hydroxy-2-methyl-5-amino-6-chlorobenzene; and heterocyclic derivatives such as: 3,4-dihydro-2H-1,4-benzoxazin-6-ol, 4-methyl-2-phenyl-2,4-dihydro-3H-pyrazol-3-one, 6-methoxyquinolin-8-amine, 4-methylpyridine-2,6-diol, 2,3-dihydro-1,4-benzodioxin-5-ol, 1,3-benzodioxol-5-ol, 2-(1,3-benzodioxol-5-ylamino)ethanol, 3,4-dimethylpyridine-2,6-diol, 5-chloropyridine-2,3-diol, 2,6-dimethoxypyridine-3,5-diamine, 1,3-benzodioxol-5-amine, 2-{[3,5-diamino-6-(2-hydroxyethoxy)-pyridin-2-yl]oxy}-ethanol, 1H-indol-4-ol, 5-amino-2,6-dimethoxypyridin-3-ol, 1H-indole-5,6-diol, 1H-indol-7-ol, 1H-indol-5-ol, 1H-indol-6-ol, 6-bromo-1,3-benzodioxol-5-ol, 5-aminopyridin-3-ol, pyridine-2,6-diamine, 3-[(3,5-diaminopyridin-2-yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine; 3,4-dihydro-2H-1,4-benzoxazin-6-amine; 4-hydroxy-N-methylindole, 1H-5-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo-[1,5-a]benzimidazole, 2,6-dihydroxypyridine, 2,6-dihydroxy-3,4-dimethylpyridine, 5-methylpyrazolo[5,1-e]-1,2,3-triazole, 5-methyl-6-chloropyrazolo[5,1-e]-1,2,3, -triazole, 5-phenylpyrazolo[5,1-e]-1,2,3-triazole and its addition salts, 1H-2,6-dimethylpyrazolo[1,5-b]-1,2,4-triazole tosylate, 7,8-dicyano-4-methylimidazolo-[3,2-a]imidazole, 2,7-dimethylpyrazolo[1,5-a]pyrimidin-5-one, 2,5-dimethylpyrazolo[1,5-a]pyrimidin-7-one, and 2-methyl-5-methoxymethyl-pyrazolo[1,5-a]pyrimidin-7-one; 6-Hydroxybenzomorpholine; and 3-Amino-2-methylamino-6-methoxypyridine; 1-Phenyl-3-methyl-5-pyrazolone-2,4-dihydro-5,2-phenyl-3H-pyrazole-3-one.

In another aspect of the present invention, coupler substances include, but are not limited to, N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di-[(2-hydroxyethyl)amino]-1,5-dimethoxybenzene, 2,3-diamino-6-methoxypyridine, 3-amino-6-methoxy-2-(methylamino)-pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1-(3-hydroxypropoxy)benzene, 1-(2-aminoethoxy)-2,4- diaminobenzene, 2-amino-1-(2-hydroxyethoxy)-4-methylaminobenzene, 2,4-diaminophenoxyacetic acid, 3-[di(2-hydroxyethyl)-amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di-(2,4-diaminophenoxy)methane, 1,3-diamino-2,4-dimethoxybenzene, 2,6-bis-(2-hydroxyethyl)aminotoluene, 4-hydroxyindol, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methyl-phenol, 3-amino-phenol, 2-[(3-hydroxyphenyl)amino]acetamide, 5-[(2-hydroxyethyl)amino]-2-methylphenol, 3-[(2-hydroxyethyl)amino]-phenol, 3-[(2-methoxy-ethyl)amino]-phenol, 5-amino-2-ethylphenol, 2-(4-amino-2-hydroxyphenoxy)-ethanol, 5-[(3-hydroxypropyl)amino]-2-methylphenol, 3-[(2,3-dihydroxypropyl)-amino]-2-methyl-phenol, 3-[(2-hydroxyethyl)amino]-2-methylphenol, 2-amino-3-hydroxy-pyridine, 5-amino-4-chloro-2-methylphenol, 1-naphthol, 1,5-dihydroxy-naphthalene, 1,7-dihydroxy-naphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxy-indole, 6-hydroxyindole, 7-hydroxy-indole and 2,3-indolindione, or their salts.

To produce natural shades and fashionable red tones, it is advantageous to use additional primary intermediates (developer substances), such as p-phenylenediamine derivatives, e.g. benzene-1,4-diamine (commonly known as p-phenylenediamine), 2-methyl-benzene-1,4-diamine, 2-chlorobenzene-1,4-diamine, N-phenyl-benzene-1,4-diamine, N-(2-ethoxyethyl)benzene-1,4-diamine, 2-[(4-amino-phenyl)-(2-hydroxy-ethyl)-amino]-ethanol, (commonly known as N,N-bis(2-hydroxyethyl)-p-phenylenediamine) (2,5-diamino-phenyl)-methanol, 1-(2'-Hydroxyethyl)-2,5-diaminobenzene, 2-(2,5-diamino-phenyl)-ethanol, N-(4-aminophenyl)benzene-1,4-diamine, 2,6-dimethyl-benzene-1,4-diamine, 2-isopropyl-benzene-1,4-diamine, 1-[(4-aminophenyl)amino]-propan-2-ol, 2-propyl-benzene-1,4-diamine, 1,3-bis[(4-aminophenyl)(2-hydroxyethyl)amino]propan-2-ol, $N^4,N^4$,2-trimethylbenzene-1,4-diamine, 2-methoxy-benzene-1,4-diamine, 1-(2,5-diaminophenyl)ethane-1,2-diol, 2,3-dimethyl-benzene-1,4-diamine, N-(4-amino-3-hydroxy-phenyl)-acetamide, 2,6-diethylbenzene-1,4-diamine, 2,5-dimethylbenzene-1,4-diamine, 2-thien-2-ylbenzene-1,4-diamine, 2-thien-3-ylbenzene-1,4-diamine, 2-pyridin-3-ylbenzene-1,4-diamine, 1,1'-biphenyl-2,5-diamine, 2-(methoxymethyl)-benzene-1,4-diamine, 2-(aminomethyl)benzene-1,4-diamine, 2-(2,5-diaminophenoxy)ethanol, N-[2-(2,5-diaminophenoxy)ethyl]-acetamide, N,N-dimethylbenzene-1,4-diamine, N,N-diethylbenzene-1,4-diamine, N,N-dipropylbenzene-1,4-diamine, 2-[(4-aminophenyl)-(ethyl)amino]ethanol, 2-[(4-amino-3-methyl-phenyl)-(2-hydroxy-ethyl)-amino]-ethanol, N-(2-methoxyethyl)-benzene-1,4-diamine, 3-[(4-aminophenyl)amino]propan-1-ol, 3-[(4-aminophenyl)-amino]propane-1,2-diol, N-{4-[(4-aminophenyl)amino]butyl}benzene-1,4-diamine, and 2-[2-(2-{5-[(2,5-diaminophenyl)-oxy]ethoxy}ethoxy)ethoxy]benzene-1,4-diamine; 1,3-Bis(N(2-Hydroxyethyl)-N-(4-amino-phenyl)amino)-2-propanol; 2,2'-[1,2-Ethanediyl-bis-(oxy-2,1-ethanediyloxy)]-bis-benzene-1,4-diamine; N,N-Bis(2-hydroxyethyl)-p-phenylenediamine; p-aminophenol derivatives such as: 4-amino-phenol (commonly known as p-aminophenol), 4-methylamino-phenol, 4-amino-3-methyl-phenol, 4-amino-2-hydroxymethyl-phenol, 4-amino-2-methyl-phenol, 4-amino-1-hydroxy-2-(2'-hydroxyethylaminomethyl)benzene, 4-amino-2-methoxymethyl-phenol, 5-amino-2-hydroxy-benzoic acid, 1-(5-amino-2-hydroxy-phenyl)-ethane-1,2-diol, 4-amino-2-(2-hydroxy-ethyl)-phenol, 4-amino-3-(hydroxymethyl)-phenol, 4-amino-3-fluoro-phenol, 4-amino-2-(aminomethyl)-phenol, 4-amino-2-fluoro-phenol; 1-Hydroxy-2,4-diaminobenzene; 1-(2'-Hydroxyethyloxy)-2,4-diaminobenzene; 2,4-Diamino-5-methylphenetol; o-phenylenediamine derivatives such as: 3,4-Diaminobenzoic acid and salts thereof; o-aminophenol derivatives such as: 2-amino-phenol (commonly known as o-aminophenol), 2,4-diaminophenol, 2-amino-5-methyl-phenol, 2-amino-5-ethyl-phenol, 2-amino-6-methyl-phenol, N-(4-amino-3-hydroxy-phenyl)-acetamide, and 2-amino-4-methyl-phenol; and heterocyclic derivatives such as: pyrimidine-2,4,5,6-tetramine (commonly known as 2,4,5,6-tetramino-pyridine), 1-methyl-1H-pyrazole-4,5-diamine, 2-(4,5-diamino-1H-pyrazol-1-yl)ethanol, $N^2,N^2$-dimethyl-pyridine-2,5-diamine, 2-[(3-amino-6-methoxypyridin-2-yl)amino]ethanol, 6-methoxy-$N^2$-methyl-pyridine-2,3-diamine, 2,5,6-triaminopyrimidin-4(1H)-one, pyridine-2,5-diamine, 1-isopropyl-1H-pyrazole-4,5-diamine, 1-(4-methylbenzyl)-1H-pyrazole-4,5-diamine, 1-(benzyl)-1H-pyrazole-4,5-diamine, 1-(4-chlorobenzyl)-1H-pyrazole-4,5-diamine, pyrazolo[1,5-a]-pyrimidine-3,7-diamine, 5,6,7-trimethylpyrazolo[1,5-a]pyrimidin-3-ylamine hydrochloride, 7-methylpyrazolo[1,5-a]pyrimidin-3-ylamine hydrochloride, 2,5,6,7-teramethylpyrazolo[1,5-a]pyrimidin-3-ylamine hydrochloride, 5,7-di-tert-butylpyrazolo[1,5-a]pyrimidin-3-ylamine hydrochloride, 5,7-di-trifluoromethyl-pyrazolol[1,5-a]pyrimidin-3-ylamine hydrochloride, 2-methylpyrazolo[1,5-a]pyrimidin-3,7-diamine hydrochloride; 4-hydroxy-2,5,6-triaminopyrimidine; 1-(2'hydroxyethyl)-amino-3,4-methylene dioxybenzene; and 1-hydroxyethyl-4,5-diaminopyrazole sulphate.

Additional primary intermediates (developers) include, but are not limited to, N-(3-furylmethyl)benzene-1,4-diamine; N-Thiophen-3-ylmethyl-benzene-1,4-diamine; N-(2-furylmethyl)benzene-1,4-diamine; N-Thiophen-2-ylmethyl-benzene-1,4-diamine; 4-Hydroxy-benzoic acid (2,5-diamino-benzylidene)-hydrazide; 3-(2,5-Diamino-phenyl)-N-ethyl-acrylamide; 2-[3-(3-Amino-phenylamino)-propenyl]-benzene-1,4-diamine; 2-[3-(4-Amino-phenylamino)-propenyl]-benzene-1,4-diamine; 2-(6-Methyl-pyridin-2-yl)-benzene-1,4-diamine; 2-Pyridin-2-yl-benzene-1,4-diamine; 2-[3-(4-Amino-phenylamino)-propenyl]-benzene-1,4-diamine; 2-[3-(3-Amino-phenylamino)-propenyl]-benzene-1,4-diamine; 3-(2,5-Diamino-phenyl)-N-ethyl-acrylamide; 2-Thiazol-2-yl-benzene-1,4-diamine; 4-Hydroxy-benzoic acid (2,5-diamino-benzylidene)-hydrazide; 3'-Fluoro-biphenyl-2,5-diamine; 2-Propenyl-benzene-1,4-diamine; 2'-Chloro-biphenyl-2,5-diamine; N-Thiophen-3-ylmethyl-benzene-1,4-diamine; N-(3-furylmethyl)benzene-1,4-diamine; 4'-Methoxy-biphenyl-2,5-diamine; N-(4-Amino-benzyl)-benzene-1,4-diamine; 2-Methyl-5-[(1-H-pyrrol-2-ylmethyl)-amino]-phenol; 5-[(Furan-2-ylmethyl)-amino]-2-methyl-phenol; 5-Isopropylamino-2-methyl-phenol;

Biphenyl-2,4,4'-triamine hydrochloride; 5-(4-Amino-phenyl)aminomethyl-benzene-1,3-diamine hydrochloride; 5-Phenylaminomethyl-benzene-1,3-diamine hydrochloride; 2-[4-Amino-2-(3,5-diamino-benzylamino)-phenoxy]-ethanol hydrochloride; 5-(3-Amino-phenyl)aminomethyl-benzene-1,3-diamine hydrochloride; N-(2-Amino-benzyl)-benzene-1,3-diamine hydrochloride; N-Furan-2-ylmethyl-benzene-1,3-diamine hydrochloride; 2-[(3-Amino-phenylamino)-methyl]-phenol hydrochloride; 4-Amino-2-propylaminomethyl-phenol hydrochloride; N-Benzo[1,3]dioxol-5-ylmethyl-benzene-1,3-diamine hydrochloride; N-[4-Amino-2-(2-hydroxyethyl)-2H-pyrazol-3-yl]-3-(5-amino-2-hydroxy-phenyl)-acrylamide hydrochloride; 4-Amino-2-(isopropylamino-methyl)-phenol hydrochloride; 4-Thiophen-3-yl-benzene-1,3-diamine hydrochloride; 5-Phenylaminomethyl-benzene-1,3-diamine hydrochloride; 5-(3-Amino-phenyl)aminomethyl-benzene-1,3-diamine hydrochloride; 4-Thiophen-3-yl-benzene-1,3-diamine hydrochloride; 2',4'-Diamino-biphenyl-4-ol hydrochloride; 5-Cyclobutylamino-2-methyl-phenol; 5-Cyclobutylamino-2-methyl-phenol; 4-Amino-2-(pyridin-3-ylaminomethyl)-phenol; 5-(3-Amino-phenyl)aminomethyl-benzene-1,3-diamine hydrochloride; 5-Allylaminomethyl-benzene-1,3-diamine hydrochloride; N-(4-Amino-benzyl)-benzene-1,3-diamine hydrochloride; N-Benzyl-benzene-1,3-diamine hydrochloride; 3-[(3-Amino-phenylamino)-methyl]-phenol hydrochloride; N-(4-Methoxy-benzyl)-benzene-1,3-diamine hydrochloride; N-Thiophen-2-ylmethyl-benzene-1,3-diamine hydrochloride; 4-Amino-2-[(2-hydroxy-5-nitro-phenylamino)-methyl]-phenol hydrochloride; 2',4'-Diamino-biphenyl-4-ol hydrochloride; Biphenyl-2,4,4'-triamine; 5-(4-Amino-phenyl)aminomethyl-benzene-1,3-diamine hydrochloride; 2-[4-Amino-2-(3,5-diamino-benzylamino)-phenoxy]-ethanol hydrochloride; 5-Allylaminomethyl-benzene-1,3-diamine hydrochloride; 5-(3-Amino-phenyl)aminomethyl-benzene-1,3-diamine hydrochloride; N-(4-Amino-benzyl)-benzene-1,3-diamine hydrochloride; N-Benzyl-benzene-1,3-diamine hydrochloride; 3-[(3-Amino-phenylamino)-methyl]-phenol hydrochloride; N-(2-Amino-benzyl)-benzene-1,3-diamine hydrochloride; N-(4-Methoxy-benzyl)-benzene-1,3-diamine hydrochloride; N-Furan-2-ylmethyl-benzene-1,3-diamine hydrochloride; 2-[(3-Amino-phenylamino)-methyl]-phenol hydrochloride; N-Thiophen-2-ylmethyl-benzene-1,3-diamine hydrochloride; N-Benzol[1,3]dioxol-5-ylmethyl-benzene-1,3-diamine hydrochloride; N-[4-Amino-2-(2-hydroxy-ethyl)-2H-pyrazol-3-yl]-3-(5-amino-2-hydroxy-phenyl)-acrylamide hydrochloride; 4-Amino-2-propylaminomethyl-phenol hydrochloride; 4-Amino-2-(isopropylamino-methyl)-phenol hydrochloride; 4-Amino-2-[(2-hydroxy-5-nitro-phenylamino)-methyl]-phenol hydrochloride; 2-Methyl-5-[(1-H-pyrrol-2-ylmethyl)-amino]-phenol; 5-[(Furan-2-ylmethyl)-amino]-2-methyl-phenol; 5-Isopropylamino-2-methyl-phenol; 5-Cyclobutylamino-2-methyl-phenol; 4-Amino-2-(pyridin-3-ylaminomethyl)-phenol; and 5-Cyclobutylamino-2-methylphenol.

The following compounds can be employed in the composition of the present invention as primary intermediates (developer compounds): 1,4-diamino-2,6-dimethylbenzene, 1,4-diamino-2,5-dimethylbenzene, 1,4-diamino-2,3-dimethylbenzene, 2-chloro-1,4-diaminobenzene, 4-phenylaminoaniline, 4-dimethylaminoaniline, 4-diethylamino-aniline, 4-[di(2-hydroxyethyl)amino]aniline, 4-[(2-methoxyethyl)amino]-aniline, 4-[(3-hydroxypropyl)amino]aniline, 1,4-diamino-2-(2-hydroxyethyl)benzene, 1,4-diamino-2-(1-methylethyl)benzene, 1,3-bis-[(4-aminophenyl)-(2-hydroxyethyl)amino]-2-propanol, 1,8-bis-(2,5-diaminophenoxy)-3,6-dioxaoctane, 4-aminophenol, 4-amino-3-methylphenol, 4-methyl-aminophenol, 4-amino-2-(aminomethyl)phenol, 4-amino-2-[(2-hydroxyethyl)amino]-methylphenol, 4-amino-2-(methoxymethyl)phenol, 4-amino-2-(2-hydroxyethyl)phenol, 5-amino-s alicylic acid, 2,5-diaminopyridine, 2,4,5,6-tetramino-pyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)-methyl]-1H-pyrazole, 1-[(4-chlorophenyl)methyl]-4,5-diamino-1H-pyrazole, 4,5-diamino-1-methyl-1H-pyrazole, 4,5-diamino-3-methyl-1-phenyl-1H-pyrazole, 4,5-diamino-1-(2-hydroxyethyl)-3-methyl-1H-pyrazole, 2-amino-phenol, 2-amino-6-methylphenol, 2-amino-5-ethyl-phenol, 2-methoxymethyl, 1-4-diaminobenzene and 2-amino-5-methyl-phenol, or their salts, and in any combination thereof.

The hair dyeing compositions disclosed herein can include nonoxidative hair dyes, also referred to as direct dyes. Nonoxidative hair dyes can be used alone or in combination with the above described oxidative dyes. Such direct dyes include direct-dyeing anionic, cationic or non-ionic dye compounds, such as azo or anthraquinone dyes and nitro derivatives of the benzene series and mixtures thereof. Direct dyes are useful to deliver shade modification or highlights.

Nonoxidative dyes can be present in the dyeing composition in an amount between 0.001% to 20% by weight, based on the weight of the composition as a whole. In another aspect nonoxidative dyes can be present in the dyeing composition in an amount between 0.001% to 10% by weight, based on the weight of the composition as a whole. Yet, in another aspect nonoxidative dyes can be present in the dyeing composition in an amount between 0.001% to 8% by weight, based on the weight of the composition as a whole. Still, in another aspect nonoxidative dyes can be present in the dyeing composition in an amount between 0.005% to 5% by weight, based on the weight of the composition as a whole. Still yet, in another aspect nonoxidative dyes can be present in the dyeing composition in an amount between 0.01% to 2.5% by weight, based on the weight of the composition as a whole. Yet still, in another aspect nonoxidative dyes can be present in the dyeing composition in an amount between 0.01% to 2% by weight, based on the weight of the composition as a whole. Still further, in another aspect nonoxidative dyes can be present in the dyeing composition in an amount between 0.01% to 1% by weight, based on the weight of the composition as a whole. Additionally, the dying composition can have one or more oxidative die precursors present in an amount of 0.005, 0.001, 0.01, 1, 2, 3, 4, 5, 6, 7, 8, 9, 10, 11, 12, 13, 14, 15, 16, 17, 18, 19, 20% or any range between any of these numbers, by weight, based on the weight of the composition as a whole.

Examples of anionic direct-dyeing dye compounds for use in the compositions disclosed herein include, but are not limited to, 6-hydroxy-5-[(4-sulfophenyl)azo]-2-naphthalene sulfonic acid disodium salt (C.I. 15985; Food Yellow No. 3; FD&C Yellow No. 6), 2,4-dinitro-1-naphthol-7-sulfonic acid disodium salt (C.I. 10316; Acid Yellow No. 1; Food Yellow No. 1), 2-(indan-1,3-dion-2-yl)quinoline-x,x-sulfonic acid (mixture of mono- and disolfuonic acid) (C.I. 47005; D&C Yellow No. 10; Food Yellow No. 13, Acid Yellow No. 3), 5-hydroxy-1-(4-sulfophenyl)-4-[(4-sulfophenyl)azo]pyrazole-3-carboxylic acid sodium salt (C.I. 19140; Food Yellow No. 4; Acid Yellow No. 23), 9-(2-carboxyphenyl)-6-hydroxy-3H-xanthen-3-one (C.I. 45350; Acid Yellow No. 73; D&C Yellow No. 8), 5-[(2,4-dinitrophenyl)amino]-2-phenylaminobenzenesulfonic acid sodium salt (C.I. 10385; Acid Orange No. 3), 4-[(2,4-dihydroxyphenyl)azo]-benzene sulfonic acid monosodium salt (C.I. 14270; Acid Orange No. 6), 4-[(2- hydroxynaphth-1-yl)azo]benzenesulfonic acid sodium salt (C.I. 15510; Acid Orange No. 7), 4-[(2,4-dihydroxy-3-[(2,4-dimethylphenyl)azo]phenyl)azo]-benzene sulfonic acid sodium salt (C.I. 20170; Acid Orange No. 24), 4-hydroxy-3-[(4-sulfonaphth-1-yl)azo]-1-naphthalene sulfonic acid disodium salt (C.I. 14720; Acid Red No. 14), 6-hydroxy-5-[(4-sulfonaphth-1-yl)azo]-2,4-naphthalene-disulfonic acid trisodium salt (C.I. 16255; Ponceau 4R; Acid Red No. 18), 3-hydroxy-4-[(4-sulfonaphth-1-yl)azo]-2,7-naphthalenedisulfonic acid trisodium salt (C.I. 16185; Acid Red No. 27), 8-amino-1-hydroxy-2-(phenylazo)-3,6-naphthalene disulfonic acid disodium salt (C.I. 17200; Acid Red No. 33), 5-(acetylamino)-4-hydroxy-3-[(2-methylphenyl)azo]-2,7-naphthalene disulfonic acid disodium salt (C.I. 18065; Acid Red No. 35), 2-(3-hydroxy-2,4,5,7-tetraiodo-dibenzopyran-6-on-9-yl)-benzene sulfonic acid disodium salt (C.I. 45430; Acid Red No. 51), N-[6-(diethylamino)-9-(2,4-disulfophenyl)-3H-xanthen-3-yliden]-N-ethyleth-anaminium hydroxide, inner Salt, sodium salt (C.I. 45100; Acid Red No. 52), 8-[(4-(phenylazo)phenyl)azo]-7-naphthol-1,3-disulfonic acid disodium salt (C.I. 27290; Acid Red No. 73), 2',4',5',7'-tetrabromo-3',6'-dihydroxyspiro[isobenzofuran-1-(3H), 9'-[9H]xanthen]-3-one disodium salt (C.I. 45380; Acid Red No. 87), 2',4',5',7'-tetrabromo-4,5,6,7-tetrachloro-3',6'-dihydroxyspiro[isobenzofuran-1-(3H), 9'[9H]xanthen]-3-one disodium salt (C.I. 45410; Acid Red No. 92), 3',6'-dihydroxy-4', 5'-diiodospiro[isobenzofuran-1-(3H), 9'[9H]xanthen)-3-one disodium salt (C.I. 45425; Acid Red No. 95), (2-sulfophenyl)-di-4-(ethyl-((4-sulfophenyl)methyl)-amino]phenyl]carbenium disodium salt, betaine (C.I. 42090; Acid Blue No. 9; FD&C Blue No. 1), 1,4-bis-[(2-sulfo-4-methyl-phenyl) amino]-9,10-anthraquinone disodium salt (C.I. 61570; Acid Green No. 25), bis-[4-(dimethylamino)phenyl]-(3,7-disulfo-2-hydroxynaphth-1-yl)carbenium inner salt, monosodium salt (C.I. 44090; Food Green No. 4; Acid Green No. 50), bis[4-(diethylamino)phenyl](2,4-disulfophenyl)carbenium inner salt, sodium salt (2:1) (C.I. 42045; Food Blue No. 3; Acid Blue No. 1), bis[4-(diethylamino)phenyl]-(5-hydroxy-2,4-disulfophenyl)carbenium inner salt, calcium salt (2:1) (C.I. 42051; Acid Blue No. 3), 1-amino-4-(cyclohexylamino)-9,10-anthraquinone-2-sulfonic acid sodium salt (C.I. 62045; Acid Blue No. 62), 2-(1,3-dihydro-3-oxo-5-sulfo-2H-indol-2-yliden)-2,3-dihydro-3-oxo-1H-indo-1-5-sulfonic acid disodium salt (C.I. 73015; Acid Blue No. 74), 9-(2-carboxyphenyl)-3-[(2-methylphenyl)-amino]6-[(2-methyl-4-sulfophenyl)-amino]xanthylium inner salt, monosodium salt (C.I. 45190; Acid Violet No. 9), 1-hydroxy-4-[(4-methyl-2-sulfophenyl)amino]-9,10-anthraquinone sodium salt (C.I. 60730; D&C Violet No. 2; Acid Violet No. 43), bis-[3-nitro-4-[(4-phenylamino)-3-sulfophenylamino]phenyl]-sulfone (C.I. 10410; Acid Brown No. 13), 5-amino-4-hydroxy-6-[(4-nitrophenyl)azo]3-(phenylazo)-2,7-naphthalene disulfonic acid disodium salt (C.I. 20470; Acid Black No. 1), 3-hydroxy-4-[(2-hydroxynaphth-1-yl)azo]-7-nitronaphthalenesulfonic acid chromium complex (3:2) (C.I. 15711; Acid Black No. 52), 3-[(2,4-dimethyl-5-sulfophenyl) azo]-4-hydroxy-1-naphthalene-sulfonic acid disodium salt (C.I. 14700; Food Red No. 1; Ponceau SX; FD&C Red No. 4), 4-(acetylamino)-5-hydroxy-6-[(7-sulfo-4-[(4-sulfophenyl) azo]naphth-1yl)azo]-1,7-naphthalene disulfonic acid tetrasodium salt (C.I. 28440; Food Black No. 1), 3-hydroxy-4-(3-methyl-5-oxo-1-phenyl-4,5-dihydro-1H-pyrazole-4-yl-azo)-naphthalene-1-sulfonic acid sodium salt chromium complex (Acid Red No. 195).

Cationic direct-dyeing dye compounds include, but are not limited to, 9-(dimethylamino)-benzo[a]phenoxazin-7-ium chloride (C.I. 51175; Basic Blue No. 6), di[4-(diethylamino) phenyl]-[4-(ethylamino)naphthyl]carbenium chloride (C.I. 42595; Basic Blue No. 7), 3,7-di(dimethylamino)phenothiazin-5-ium chloride (C.I. 52015; Basic Blue No. 9), di[4-dimethylamino)phenyl][4(phenylamino)naphthyl]carbenium chloride (C.I. 44045; Basic Blue No. 26), 2-[(4-(ethyl (2-hydroxyethyl)amino)phenyl)azo]-6-methoxy-3-methylbenzothiazolium methylsulfate (C.I. 11154; Basic Blue No. 41), 8-amino-2-bromo-5-hydroxy-4-imino-6-[(3-(trimethylammonio)phenyl)amino]-1-(4H)naphthalenone chloride (C.I. 56059; Basic Blue No. 99), bis-[4-(dimethylamino)phenyl][4-(methylamino)phenyl]carbenium chloride (C.I. 42535; Basic Violet No. 1) tris-(4-amino-3-methylphenyl) carbenium chloride (C.I. 425 20; Basic Violet No. 2), tris-[4-(dimethylamino)phenyl]carbenium chloride (C.I. 42555; Basic Violet No. 3), 2-[3,6-(diethylamino)dibenzopyranium-9-yl]benzoic acid chloride (C.I. 45170; Basic Violet No. 10), di(4-aminophenyl)(4-amino-3-methylphenyl)carbenium chloride (C.I. 42510; Basic Violet No. 14), 1,3-bis[(2,4-diamino-5-methylphenyl)azo]-3-methylbenzene (C.I. 21010; Basic Brown No. 4), 1-[(4-aminophenyl)azo]-7-(trimethylammonio)-2-naphthol chloride (C.I. 12250; Basic Brown No. 16), 1-[(4-amino-2-nitrophenyl)azo]-7-(trimethylammonio)-2-naphthol chloride (C.I. 12251; Basic Brown No. 17), 1-[(4-amino-3-nitrophenyl)azo]-7-(trimethylammonio)-2-naphthol chloride (C.I. 12251; Basic Brown No. 17), 3,7-diamino-2,8-dimethyl-5-phenylphenazinium chloride (C.I. 50240; Basic Red No. 2), 1,4-dimethyl-5-[(4(dimethylamino)phenyl)azo]-1,2,4-triazolium chloride (C.I. 11055; Basic Red No. 22), 2-hydroxy-1-[(2-methoxyphenyl)azo]-7-(trimethylammonio)naphthalene chloride (C.I. 12245; Basic Red No. 76), 2-[2-((2,4-dimethoxyphenyl)amino)ethenyl]-1, 3,3-trimethyl-3H-indol-1-ium-chloride (C.I. 48055; Basic Yellow No. 11), 3-methyl-1-phenyl-4-[(3-(trimethylammonio)phenyl)azo]-pyrazole-5-one chloride (C.I. 12719; Basic Yellow No. 57), bis[4-(diethylamino)phenyl]phenylcarbenium hydrogen sulfate (1:1) (C.I. 42040; Basic Green No. 1).

Nonionic direct-dyeing dye compounds, which can be used to improve the color balance and produce special shades, include, but are not limited to, 1-amino-2-[(2-hydroxyethyl) amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-ureidoethyl)amino]-4-nitrobenzene, 4-[(2,3-dihydroxypropyl)amino]-3-nitro-1-trifluoromethylbenzene (HC Yellow No. 6), 1-chloro-2,4-bis-[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)-amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 1-amino-4-[(2-hydroxyethyl)amino]-2-nitrobenzene (HC Red No. 7), 2-amino-4,6-dinitrophenol, 2-ethylamino-4,6-dinitrophenol, 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2hydroxyethyl)amino]-2-nitrobenzene, 4-amino-1-[(2-hydroxyethyl)-amino]-2-nitrobenzene (HC Red No. 3), 4-amino-3-nitrophenol, 4-[(2-hydroxyethyl)amino]-3-nitrophenol, 1-[(2-aminoethyl)amino]4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)-amino]-4,6-dinitrophenol, 4-ethylamino-3-nitrobenzoic acid, 2-[(4-amino-2-nitrophenyl)amino]-benzoic acid, 2-chloro-6-methylamino-4-nitrophenol 2-chloro-6-[(2-hydroxyethyl)amino]4-nitrophenol, 2-chloro-6-ethylamino-4-nitrophenol, 2-amino-6-chloro-4-nitrophenol, 4-[(3-hydroxypropyl)-amino]-3-nitrophenol, 2,5-diamino-6-nitropyridine, 1,2,3,4-tetrahydro-6-nitrochinoxalin, 7-amino-3,4-dihydro-6-nitro-2H-1,4-benzoxazine (HC Red No. 14), 1,4-bis-[(2-hydroxyethyl)-amino]-2-nitrobenzene, 1-(2-hydroxyethyl)amino-2-nitro-4-[di(2-hydroxyethyl)amino]benzene (HC Blue No. 2), 1-amino-3-methyl-4-[(2-hydroxyethyl)amino]-6-nitrobenzene (HC Violet No. 1), 4-[ethyl-(2-hydroxyethyl)amino]-1-[(2-hydroxyethyl)amino]-2-nitrobenzene hydrochloride (HC Blue No. 12), 4-[di(2-hydroxyethyl)amino]-1-[(2-methoxyethyl) amino]-2-nitrobenzene (HC Blue No. 11), 1-[(2,3-dihydroxy-propyl)amino]4-[methyl-(2-hydroxyethyl)amino]-2-nitrobenzene (HC Blue No. 10), 1-[(2,3-dihydroxypropyl) amino]4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene (HC Violet No. 2), 1-methylamino-4-[methyl-(2,3-dihydroxypropyl) amino]-2nitrobenzene (HC Blue No. 6), 2-((4-amino-2-nitrophenyl)amino)-5-dimethylamino-benzoic acid (HC Blue No. 13), 1,4-di[(2,3-dihydroxypropyl)amino]-9,10-anthraquinone, 1-[(2-hydroxyethyl)amino]4-methylamino-9,10-anthraquinone (C.I. 61505, disperse Blue No. 3), 2-[(2-aminoethyl)amino]-9,10-anthraquinone (HC Orange No. 5), 1-hydroxy-4-[(4-methyl-2-sulfophenyl)amino]-9,10-anthraquinone, 1-[(3-aminopropyl)amino]-4-methylamino-9,10-anthraquinone (HC Blue No. 8), 1-[(3-aminopropyl) amino]-9,10-anthraquinone (HC Red No. 8), 1,4-diamino-2-methoxy-9,10-anthraquinone (C.I. 62015, disperse Red No. 11, Solvent Violet No. 26), 1,4-dihydroxy-5,8-bis[(2-hydroxyethyl)amino-9,10-anthraquinone (C.I. 62500, disperse Blue No. 7, Solvent Blue No. 69), 1-[di-(2-hydroxyethyl) amino]-3-methyl-4-[(4-nitrophenyl)azo]benzene (C.I. 11210, disperse Red No. 17), 4-[(4-aminophenyl)azo]-1-[di (2-hydroxyethyl)amino]-3-methylbenzene (HC Yellow No. 7), 2,6-diamino-3-[(pyridine-3-yl)azo]pyridine, 2-((4-(acetylamino)phenyl)-azo)-4-methylphenol (C.I. 11855; disperse Yellow No. 3).

Additional direct-dyeing dye compounds include, but are not limited to, 2-amino-4,6-dinitrophenol, 2-ethylamino-4,6-dinitrophenol, 2-[(2-hydroxyethyl)-amino]-4,6-dinitrophenol and dye compounds of the following general formula (V):

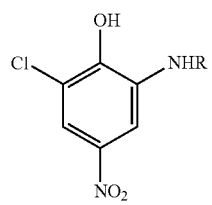

wherein R represents hydrogen, methyl, ethyl or hydroxyethyl.

As discussed above, hair dyeing compositions disclosed herein can comprise from about 0.001% to about 20% by weight of direct dyes. In another aspect, hair dyeing compositions of the present invention comprise from about 0.1% to about 10% by weight. Yet, in another aspect, hair dyeing compositions of the present invention comprise from about 0.2% to about 5% by weight. Still further, hair dyeing composition of the present invention can comprise up to 50% by weight of direct dyes.

The keratin fiber dyeing compositions, for example hair dyeing compostions, disclosed herein can employ fluorescent dyes. Fluorescent dyes comprise molecules that color by themselves and absorb light in the visible and possibly the ultraviolet spectrum (wavelengths ranging from 360 to 760 nanometers). In contrast to a standard dye, fluorescent dyes convert the absorbed energy into fluorescent light of longer wavelength emitted in the visible region of the spectrum.

Example fluorescent dyes useful with the compositions disclosed herein include, but are not limited to, fluorescent dyes belonging to the following families: naphthalimides; cationic or non-cationic coumarins; xanthenodiquinolizines (such as, sulphorhodamines); azaxanthenes; naphthol actams; azlactones; oxazines; thiazines; dioxazines; polycationic fluorescent dyes of azo, azomethine or methine type, alone or as mixtures.

When employed, the fluorescent dye(s) represent(s) from 0.01% to 20% by weight, relative to the total weight of the composition. In another aspect, the fluorescent dye(s) can be present in an amount from 0.05% to 10% by weight. Yet, in another aspect, the fluorescent dye(s) can be present in an amount from 0.1% to 5% by weight. Further, the fluorescent dye(s) can be present in an amount up to 40% by weight.

Liposoluble dyes include, but are not limited to, soybean oil, Sudan brown, DC Yellow 11, DC Orange 5, quinoline yellow, Sudan Red 111 (CTFA name D&C red 17), lutein, quinizarine green (CTFA name DC green 6), Alizurol SS purple (CTFA name DC violet No. 2), DC Blue No. 14, carotenoid derivatives, for instance lycopene, beta-carotene, bixin or capsanthin, annatto, and/or mixtures thereof. The liposoluble dyes, when present, generally have a concentration ranging up to 30% by weight of the total weight of the hair dyeing composition. Typically, when present in the compositions disclosed herein, the liposoluble dyes are present in an amount from about 0.0001% to about 6% by weight, based on the weight of the composition. In another aspect, liposoluble dyes can be present in the composition in an amount ranging up to 6%, up to 10%, or up to 30% by weight, based on the weight of the composition Water-soluble dyes useful in the keratin fiber dyeing compositions disclosed herein include dyeing plant extracts. Dyeing plant extracts include, but are not limited to, Aleurites moluccana Wild, Alkanna tinctoria Tausch, Areca catechu L., Arrabidaea chica E. and B., Bixa orellana L (annatto), Butea monosperma Lam, Caesalpina echinata Lam, Caesalpina sappan L., Calophyllum inophyllum L., Carthamus tinctorius L., Cassia alata L., Chrozophora tinctoria L., Crocus sativus L., Curcuma longa L., Diospyros gilletii Wild, Eclipta prostrata L., Gardenia erubescens Stapf and Hutch., Gardenia terniflora Schum. and Thonn., Genipa americana L., Genipa brasiliensis L., Guibourtia demeusei (Harms) J. Leon, Haematoxylon campechianum L., Helianthus annuus, Humiria balsamifera (Aubl) St-Hil, Isatis tinctoria L., Mercurialis perenis, Monascus purpureus, Monascus ruber, Monascus pilosus, Morus nigra L., Picramnia spruceana, Pterocarpus erinaceus Poir., Pterocarpus soyauxii Taub., Rocella tinctoria L., Rothmannia whitfieldii (Lindl) Dand., Schlegelia violacea (Aubl) Griseb., Simira tinctoria Aublet, Stereospermum kunthianum Cham, Symphonia globulifera L., Terminalia catappa L., sorghum, Aronia melanocarpa, naphthoquinones including lawsone, derived from Lawsonia

*inermis* L., also known as henna, or from *Impatiens balsamina*, red wood extracts as described in document WO 98/44902, beetroot juice, the disodium salt of suschin, anthocyans, for instance extracts of red berries, dihydroxyacetone, monocarbonyl or polycarbonyl derivatives such as isatin, alloxan, ninhydrin, glyceraldehyde, mesotartaric aldehyde, pyrazoline-4,5-dione derivatives, and mixtures thereof, these skin-coloring agents optionally being combined with direct dyes or indole derivatives, and/or mixtures thereof.

Dyeing plant extracts can be in the form of a lyophilizate, a paste or a solution. The lyophilizate can be formed by grinding the leaves of the dyeing plant to obtain a powder. This powder is dissolved in an aqueous phase for several hours to form a mixture. The mixture is subsequently centrifuged and filtered. The filtrate obtained is frozen and then lyophilized Nacreous pigments can be employed in the hair dyeing compositions disclosed herein. Such pigments include, but are not limited to, white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, can be present in the composition in an amount ranging up to 60% by weight of the total composition. In another aspect, the nacreous pigments can be present in an amount from 0.1% to 20% by weight of the total composition. Still, in another aspect, the nacreous pigments can be present in an amount from 0.1% to 15% by weight of the total composition.

The pigments, which may be used according to the present invention, can be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, silica, ferric blue, lead acetate, and mixtures thereof. Representative examples of organic pigments include carbon black, pigments of D & C type, and lakes based on cochineal carmine, bariumn strontium, calcium, and aluminum. Other examples of pigments are ultramarines, HC Blue No. 14, Ext. Yellow 7, Yellow 10 Lake, and acid violet 43.

If present, the pigments can be in the composition in a concentration ranging up to 60% by weight of the composition. In another aspect, the pigments can be present in an amount from 0.01% to 60% by weight of the total composition. Yet, in another aspect, the pigments can be present in an amount from 0.01% to 30% by weight of the total composition. Still, in another aspect, the nacreous pigments can be present in an amount from 0.01% to 20% by weight of the total composition. Yet still, in another aspect, the pigments can be present in an amount from 0.01% to 10% by weight of the total composition.

The keratin fiber dyeing composition, for example the hair dyeing composition, can comprise a coloring polymer, i.e. a polymer comprising at least one organic coloring group. The coloring polymer generally contains less than 10% by weight of colorant relative to the total weight of the polymer.

The coloring polymer can be of any chemical nature, such as, a polyester, polyamide, polyurethane, polyacrylic, poly (meth)acrylic, polycarbonate, polymers of natural origin, for instance cellulose polymers or chitosan polymers, or mixtures thereof, and preferably polyester or polyurethane polymers. Also, the coloring polymer can be a copolymer based on at least two different monomers, at least one of which is an organic coloring monomer.

The monomers of the coloring polymer can be chosen from anthraquinones, methines, bis-methines, aza-methines, arylidenes, 3H-dibenzo[7,i-j]isoquinolines, 2,5-diarylaminoterephthalic acids and esters thereof, phthaloylphenothiazines, phthaloylphenoxazines, phthaloylacridone, anthrapyrimidines, anthrapyrazoles, phthalocyanins, quinophthalones, indophenols, perinones, nitroarylamines, benzodifurans, 2H-1-benzopyran-2-ones, quinophthalones, perylenes, quinacridones, triphenodioxazines, fluoridines, 4-amino-1,8-naphthalimides, thioxanthrones, benzanthrones, indanthrones, indigos, thioindigos, xanthenes, acridines, azines and oxazines. Coloring monomers are described in U.S. Pat. Nos. 4,267,306; 4,359,570; 4,403,092, 4,617,373; 4,080,355; 4,740,581; 4,116,923; 4,745,173; 4,804,719; 5,194,463 and 5,804,719 and PCT Publication WO-A-92/07913, the content of which is incorporated into the present patent application by reference.

Polymeric colorants are described in U.S. Pat. Nos. 4,804,719; 5,032,670; 4,999,418; 5,106,942; 5,030,708; 5,102,980; 5,043,376 and 5,194,463 and PCT Publications WO-A-92/07913 and WO-A-97/24102, the contents of which are herein incorporated by reference.

The coloring polymers can be present in the hair dyeing compositions in an amount ranging from about 0.01% to about 60% by weight of the composition. In another aspect, the coloring polymers can be present in the compositions in an amount from about 0.5% to about 25% by weight of the composition. Still, in another aspect, coloring polymers can be present in the hair dyeing compositions in an amount from about 0.2% to about 20% by weight of the composition.

Additional non-limiting examples of dyes useful with the present invention are disclosed in U.S. Pat. Nos. 7,766,977; 7,699,897; 7,658,771; 7,758,658; 7,749,284; 7,494,514; 7,141,079; 7,122,062; 7,094,262; 7,083,655; 6,740,130; 6,139,853 and 5,951,718, and U.S. Patent Application Publication Nos. US 2010/0150858 and US 2010/0146716, the contents of which are herein incorporated by reference.

Hair dyeing compositions disclosed herein comprise from about 0.001% to about 10% by weight of dyes. For example compositions providing low intensity dyeing such as natural blonde to light brown hair shades generally comprise from about 0.001% to about 5% by weight of dyeing composition of precursors and couplers. In another aspect of the present invention, the hair dyeing compositions comprise from about 0.1% to about 2% by weight of dyeing composition. Yet, in another aspect of the present invention, the hair dyeing compositions comprise from about 0.2% to about 1% by weight of dyeing composition of precursors and couplers. Darker shades such as browns and black typically comprise from 0.001% to about 10% by weight of precursors and couplers. In another aspect of the present invention, the hair dyeing compositions comprise from about 0.05% to about 7% by weight of dyeing composition. Yet, in another aspect of the present invention, hair dyeing compositions for darker shades comprise from about 1% to about 5% by weight of dyeing composition of precursors and couplers.

Oxidizing Agent

Keratin fiber dyeing compositions, such as hair dyeing compositions, disclosed herein can comprise an oxidizing agent. In one aspect, oxidizing agents are water-soluble peroxygen oxidizing agents. "Water-soluble" as defined herein means that in standard condition at least 0.1 g of oxidizing agent can be dissolved in 1 liter of deionized water. In another aspect, at least 1 g of oxidizing agent can be dissolved in 1 liter of deionized water. Yet, in another aspect, at least 10 g of oxidizing agent can be dissolved in 1 liter of deionized water. Oxidizing agents are employed for the initial solubilization and decolorisation of the melanin (bleaching) and accelerate the oxidation of the oxidative dye precursors (oxidative dyeing) in the hair shaft.

Any oxidizing agent known in the art can be utilized in the present invention. For example, water-soluble oxidizing agents can be inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts can be incorporated as monohydrates, tetrahydrates, etc. Also, alkyl and aryl peroxides and or peroxidases can be used. Mixtures of two or more such oxidizing agents can be used, if desired. The oxidizing agents can be provided in aqueous solution or as a powder which is dissolved prior to use. In one aspect of the present invention, the hair dyeing compositions comprise peroxymoncarbonate ions. Peroxymoncarbonate ions can be formed in-situ from hydrogen peroxide and a carbonate ion source. When peroxymoncarbonate ions are employed in combination with an alkalizing agent and the specific dyes defined hereinafter, at a pH of up to and including 9.5 can deliver further improvements of the desired hair color results and reduce the odor of and the damage to the hair fibers.

The hair dyeing compositions disclosed herein comprise from about 0.1% to about 10% by weight of the oxidizing agent. In another aspect, the hair dyeing composition comprises from about 1% to about 7% by weight of an oxidizing agent. Yet, in another aspect, the hair dyeing composition comprises from about 2% to about 6% by weight of an oxidizing agent.

Carbonate Ion Source

Hair dyeing compositions disclosed herein can comprise a source of carbonate ions or carbamate ions or hydrocarbonate ions or any mixture thereof. Any source of these ions can be utilized. Suitable sources for use herein include, but are not limited to, sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts can be utilized to provide both the source of carbonate ions and oxidizing agent.

Hair dyeing compositions disclosed herein can comprise from about 0.1% to about 5% by weight of the carbonate hydrogen carbonate or carbonate ion source ion. In another aspect, the hair dyeing compositions can comprise from about 0.1% to about 10% by weight of the carbonate hydrogen carbonate or carbonate ion source ion. Yet, in another aspect, the hair dyeing compositions can comprise from about 1% to about 8% by weight of the carbonate hydrogen carbonate or carbonate ion source ion. If present, the ammonium ions and carbonate ions are present in the composition at a weight ratio of from 3:1 to 1:10. In another aspect, if present, the ammonium ions and carbonate ions are present in the composition at a weight ratio of from 2:1 to 1:5. The ammonium ions and carbonate ion sources can be provided by a single source such as ammonium carbonate, ammonium hydrogen carbonate, ammonium hydrocarbonate or mixtures thereof.

Alkalizing Agent

The keratin dyeing compositions, for example hair dyeing compositions, disclosed herein can comprise an alkalizing agent. The alkalizing agent can be a source of ammonium ions and or ammonia. Any agent known in the art can be used, such as alkanolamides. Alkanolamides include, but are not limited to, monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol and guanidium salts. Further, any source of ammonium ions is suitable for use herein Ammonium ion sources include, but are not limited to, ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof.

The hair dyeing compositions can comprise from about 0.1% to about 10% by weight of an alkalizing agent. In another aspect, the hair dyeing compositions comprise from about 0.5% to about 5% of an alkalizing agent. Yet, in another aspect, the hair dyeing compositions comprise from about 1% to about 3% of an alkalizing agent.

pH

The hair dyeing compositions disclosed herein typically have a pH of from about 8 to about 12. In another aspect, the hair dyeing compositions have a pH of from about 8 to about 10. When the composition utilizes peroxymoncarbonate ions, the pH is up to and including pH 9.5. In another aspect, when the composition utilizes peroxymoncarbonate ions, the pH is from about 9.5 to about 7.5. Yet, in another aspect, when the composition utilizes peroxymoncarbonate ions, the pH is from about 9.5 to about 8.4. Still, in another aspect, when the composition utilizes peroxymoncarbonate ions, the pH is from about 9.4 to about 8.5. Further still, in another aspect, when the composition utilizes peroxymoncarbonate ions, the pH is about 9.0.

For good lightening and good color formation, the final formulation should have a good buffering capacity or reserve alkalinity (the ability of the system to resist the pH shift that would otherwise be caused by addition of acid). Suitable buffering systems include, but are not limited to, ammonia/ammonium acetate mixtures, monoethanolamine tetrasodium pyrophosphate, isopropanolamine, citrates, and benzoic acid.

Radical Scavenger

The compositions disclosed herein can further comprise a source of radical scavenger. As used herein the term radical scavenger refers to a species that can react with a carbonate radical to convert the carbonate radical by a series of fast reactions to a less reactive species, i.e. a carbonate radical scavenger.

Radical scavengers can be selected from the classes of alkanolamines, amino sugars, amino acids, esters of amino acids and mixtures thereof. For example, the following compounds can be employed as radical scavengers: ethylamine, monoethanolamine, 2-methoxyethylamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, morpholine, piperidine, and mixtures thereof, and the salts such as the potassium, sodium and ammonium salts thereof and mixtures thereof.

The hair dyeing compositions disclosed herein comprise a radical scavenger in an amount from about 0.1% to about 10% by weight when the radical scavenger is present. In another aspect of the invention, the radical scavenger is present in an amount from about 1% to about 7% by weight. When the carbonate ion is present in the hair dye composition, the radical scavenger is present at an amount such that the weight ratio of radical scavenger to carbonate ion is from 2:1 to 1:4. Although not required, the radical scavenger is selected such that it is not an identical species as the alkalizing agent. Further, the radical scavenger can be formed in situ in the hair dyeing compositions prior to application to the hair fibers.

Surfactants

The hair dyeing compositions can comprise at least about 0.01% of a surfactant. Surfactants suitable for use herein generally have a lipophilic chain length of from about 8 to about 30 carbon atoms and can be selected from anionic, nonionic, amphoteric, zwitterionic, cationic surfactants and mixtures thereof. Surfactants can be present in the keratin fiber dyeing composition in an amount between 0.001% to 50%, 0.001% to 30%, 0.01% to 20%, 0.01% to 15% or 0.01% to 10% by weight, based on the weight of the composition.

Gel Network Thickener

Keratin fiber dyeing compositions disclosed herein, such as the hair dyeing compositions, can comprise a gel network thickener system. The gel network thickener system is defined as a thickening system comprising a ternary surfactant system comprising a) at least one surfactant or amphophile having an hydrophilic-lipophilic balance ("HLB") of 6 or less and a melting point of at least 30° C., b) at least one surfactant selected from anionic surfactants according to the formula RnXmYM, wherein R is independently selected from alkyl, alkenyl or alkylaryl groups having from 8 to 30 carbon atoms, X is independently selected from polar groups comprising at least one carbon atom and at least one oxygen or nitrogen atom, Y is an anionic group selected from carboxylates, sulphates, sulphonates or phosphates, n and m are independently 1 or 2 and M is hydrogen or a salt forming cation and mixtures thereof, or cationic surfactants selected from quaternary ammonium salts or amido-amines having at least one fatty chain comprising at least 20 carbon atoms and mixtures thereof and c) at least one non-ionic surfactant having an HLB of 7 or more, and comprising one or more polyethyleneoxide chains. The HLB of the surfactant(s) used according to the invention is the standard HLB according to Griffin as defined in J. Soc. Cosm. Chem., Vol. 5, 1954, p. 249.

The melting point of the surfactant(s) used according to the invention can be measured by a standard melting point method as described in U.S. Pharmacopeia, USP-NF General Chapter <741> "Melting range or temperature". Further, in reference to the surfactants, "solid" refers to the material state at a temperature below 30° C.

The gel network system comprises as a first surfactant, a low HLB surfactant or amphophile having an HLB of 6 or less and melting point of at least about 30° C. Representative examples include, but are not limited to, solid fatty alcohols, solid oxyethylenated fatty alcohols, solid glycol esters, solid oxyethylenated alkyl phenols, solid sorbitan esters, solid sugar esters, solid methyl glucoside esters, solid polyglycerine esters, solid alkyl glyceryl ethers, solid propylene glycol fatty acid esters, cholesterol and ceramides.

Generally, low HLB surfactants are linear or branched fatty alcohols comprising from about 14 to 30 carbon atoms, oxyethylenated fatty alcohols comprising from about 16 to 30 carbon atoms and about 2 units of ethylene oxide, glycerol fatty acid esters comprising from about 14 to 30 carbon atoms and mixtures thereof. Further, the low HLB surfactants include cetyl, stearyl, cetostearyl or behenyl alcohols, steareth-2 and glycerol monostearate.

The second surfactant of the gel network thickener system may be anionic, or cationic. Anionic surfactants are selected from surfactants according to the formula RnXmYM, wherein R is a alkyl, alkenyl or alkylaryl group having from 8 to 30 carbon atoms, X is a polar group comprising at least one carbon atom and at least one oxygen or nitrogen atom, Y is an anionic group selected from carboxylates, sulphates, sulphonates or phosphates, n and m are independently 1 or 2 and M is hydrogen or a salt forming cation and mixtures thereof.

Representative examples of anionic surfactants include salts, such as alkaline salts. Alkaline salts which can be employed in the present invention include, for example, sodium salts, ammonium salts, amine salts, amino alcohol salts and magnesium salts. Further, the anionic surfactants employed in the present invention can be selected from alkyl ether carboxylates, alkyl ether sulphates, alkyl glyceryl sulphonates, alkylamido ether sulphates, alkylarylpolyether sulphates, alkyl monoglyceride sulphates, alkyl ether sulphonates, alkylamide sulphonates, alkyl succinates, alkyl sulphosuccinates, alkyl ether sulphosuccinates, alkylamide sulphosuccinates, alkyl sulphosuccinamates, alkyl sulphoacetates, alkyl ether phosphates, acyl sarcosinates, N-acyl methylaminopropionate, acyl isethionates, N-acyltaurates, acyl lactylates, carboxyalkyl ether of alkyl polyglucosides and alkyl lecithin derivatives. The alkyl or acyl radical of all of these various compounds, for example, comprises from about 8 to 30 carbon atoms, and the aryl radical, for example, is chosen from phenyl and benzyl groups.

In another aspect, the anionic surfactants are alkyl ether phosphates, alkyl ether sulphates, alkyl glyceryl sulphonates, N-acyl amino acid derivatives, N-acyl taurates, acyl lactylates and carboxyalkyl ether of alkyl polyglucosides. Typically, although not required, the alkyl ether phosphates have in average 1 to 20 ethylene oxide units. Still, in another aspect of the invention, the alkyl ether phosphates have in average 1-10 ethylene oxide units. Yet, in another aspect of the invention, the alkyl ether phosphates have in average 1-3 ethylene oxide units.

The cationic surfactants suitable for use in the gel network thickener system can be quaternary ammonium salts or amido-amines having at least one fatty chain containing at least about 20 carbon atoms and mixture thereof. The quaternary ammonium salts have a general formula of $N^+(R^1R^2R^3R^4)X^-$, wherein, $R^1$ is a linear or branched radical comprising about 20 to 30 carbon atoms, $R^2$ is a linear or branched radical comprising about 20 to 30 carbon atoms or the same group as radicals $R^3$ to $R^4$, the radicals $R^3$ to $R^4$, can be identical or different and are linear or branched aliphatic radicals comprising from about 1 to 4 carbon atoms, and aromatic radicals such as aryl and alkylaryl, the aliphatic radicals can comprise at least one hetero atom such as oxygen, nitrogen, sulphur and halogens, the aliphatic radicals are chosen, for example, from alkyl, alkoxy and alkylamide radicals, and wherein X— is an anion selected from halides such as chloride, bromide and iodide, $(C_2-C_6)$alkyl sulphates, such as methyl sulphate, phosphates, alkyl and alkylaryl sulphonates, and anions derived from organic acids, such as acetate and lactate. In an aspect of the invention, the cationic surfactant is a behentrimonium chloride, behenamidopropyltrimonium methosulfate, stearamidopropyltrimonium chloride, arachidtrimonium chloride, or mixtures thereof.

The amido-amine has a general formula of R'¹CONH(CH$_2$)$_n$NR'²R'³, wherein R'¹ is a linear or branched radical comprising about 20 to 30 carbon atoms, the radicals R'² and R³ can be identical or different and are selected from hydrogen, linear and branched aliphatic radicals comprising from about 1 to 4 carbon atoms, and aromatic radicals such as aryl and alkylaryl, the aliphatic radicals can comprise at least one hetero atom such as oxygen, nitrogen, sulphur and halogens, the aliphatic radicals are chosen, for example, from alkyl, alkoxy and alkylamide radicals, and wherein n is integer from 1 to 4. In an aspect of the present invention, the amido-amine is behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and mixtures thereof.

Non-ionic surfactants can be employed in the gel network thickener system employed in the hair dyeing composition of the present invention. Such non-ionic surfactants include, but are not limited to, non-ionic surfactants having an HLB of 7 or more and comprising one or more polyethyleneoxide chains. For example, non-ionic surfactants comprising one or more polyethyleneoxide chains include polyoxyethylene alkyl ethers, polyethyleneglycol fatty acid esters, polyoxyethylene castor oil, polyoxyethylene hydrogenated castor oil, polyoxyethylene fatty amides and their momoethanolamine and diethanolamine derivatives and polyethoxylated fatty amines.

In another aspect, the non-ionic surfactants include polyoxyethylene alkyl ethers or polyethylene glycol fatty acid esters having at least about 25 ethylene oxide units. Still, in another aspect, the non-ionic surfactants include polyoxyethylene alkyl ethers or polyethylene glycol fatty acid esters having from about 50 to 200 ethylene oxide units. Yet, in another aspect, the non-ionic surfactants include polyoxyethylene alkyl ethers or polyethylene glycol fatty acid esters having from about 100 to 200 ethylene oxide units, for example, ceteareth-25, steareth-100, steareth-150 and steareth-200.

Also, the gel network thickening systems include the ternary combination of fatty alcohols comprising from 14 to 30 carbon atoms, an anionic surfactant selected from $C_8$-$C_{30}$ alkyl ether phosphates having from 1 to 20 ethylene oxide units and a non-ionic surfactant selected from polyoxyethylene alkyl ethers having at least 25 ethylene oxide units. Further, the anionic surfactant can have from 2 to 10 ethylene oxide units. Still further, the non-ionic surfactant alternatively can have from 100 to 200 ethylene oxide units.

More than one surfactant of each of the above identified types of the surfactants can be used. The hair dyeing compositions disclosed herein can comprise a total amount of gel network forming surfactants from about 0.5% to about 30% by weight. In another aspect, the hair dyeing compositions can comprise a total amount of gel network forming surfactants from about 3% to about 20% by weight. Still, in another aspect, the hair dyeing compositions can comprise a total amount of gel network forming surfactants from about 6% to about 15% by weight.

The hair dyeing compositions can comprises from 0.1 to 30% by weight of the low HLB surfactant, from 0.1 to 15% by weight of the ionic (i.e. anionic and or cationic surfactant) and 0.1 to 15% by weight of the non-ionic surfactant. Further, the compositions can comprise from 1 to 20% by weight of the low HLB surfactant, from 1 to 5% by weight of the ionic (i.e. anionic and or cationic) surfactant and from 0.1 to 5% by weight of the non ionic surfactant. In another aspect, the weight ratio of low HLB surfactant or amphophile to ionic surfactant to non-ionic surfactant is from about 10:1:0.1 to about 10:10:10.

Polymers

The keratin fiber dyeing compositions disclosed herein, for example the hair dyeing compositions, can further comprise about 0.01% or more of polymer. Useful polymers include, but are not limited to, associative polymers, crosslinked acrylic acid homopolymers, crosslinked copolymers of (meth)acrylic acid and of ($C_1$-$C_6$)alkyl acrylate or polysaccharides. The polymer can serve as a thickening agent. Additionally, the polymer can serve as a conditioning agent, as described below. Generally, the polymer is present in an amount from about 0.01% to about 20.0% by weight of the composition. In another aspect, the polymer is present in an amount from about 0.1% to about 5% by weight of the composition.

Conditioning Agent

Keratin fiber dyeing compositions disclosed herein, for example hair dyeing compositions, can comprise or be used in combination with a composition comprising a conditioning agent. Suitable conditioning agents include, but are not limited to silicone materials, amino silicones, fatty alcohols, polymeric resins, polyol carboxylic acid esters, cationic polymers, cationic surfactants, insoluble oils and oil derived materials, amino acids, proteins, extracts, fats, oils, esters, transesters, hydrocarbons, quats, polyquats, zwitterionic surfactants, amphoteric surfactants, alcohols, polyols, humectants, alkanolamides, fatty acids, ketones and mixtures thereof. Additional materials include mineral oils and other oils such as glycerin and sorbitol. Cationic polymer type conditioners generally comprise units of at least one amine group chosen from primary, secondary, tertiary and quaternary amine groups which either form part of the main polymer chain or comprise a side substituent directly attached to the main polymer chain.

Non-limiting examples of conditioning agents include, but are not limited to, Arginine, Asparagine, Aspartic Acid, Carnitine, Cocoyl sarcosine, Glycine, Glutamic acid, Histidine, Hydroxyproline, Acetyl Hydroxy praline, Isoleucine, Lysine, Lauroyl Lysine, Lauroyl Sarcosine, Methionine, Phenylalanine, Polylysine, Potassium Cocoyl Glutamate, Proline, Sarcosine, Serine, Rice amino acids, Silk amino acids, Wheat amino aids, Sodium Glutamate, Sodium Lauroyl Glutamate, Sodium PCA, Stearoyl sarcosine, Threonine, Tyrosine, Tryptophan, Valine, Casein, Collagen, Procollagen, Gelatin, Keratin, Glycoproteins, Hydrolyzed wheat protein, Hydrolyzed soy protein, Hydrolyzed oat protein, Hydrolyzed rice protein, Hydrolyzed vegetable protein, Hydrolyzed yeast protein, Whey protein, Ginkgo Biloba Nut extract, *Salix Alba* (Willow) Bark Extract, *Morns Alba* (Mulberry) Leaf, Behentrimonium Chloride, Behenamidopropyl PG-Dimonium Chloride, Behentrimonium Methosulfate, Cocotrimonium Methosulfate, Olealkonium Chloride, Steartrimonium Chloride, Babassuamidopropalkonium Chloride, Hydroxypropyl Guar, Hydroxypropyltrimonium chloride, Laurdimonium Hydroxypropyl Hydrolyzed Soy Protein, Steardimonium Hydroxypropyl Hydrolyzed Wheat Protein, Quaternium-22, Quaternium-27, Quaternium-87, Polyquaternium-4, Polyquaternium-6, Polyquaternium-10, Polyquaternium-11, Polyquaternium-44, Polyquaternium-67, Silicone Quaternium-8, Amodimethicone, Aminopropyldimethicone, Phenyltrimethicone, Cyclomethic one, Dimethicone, Hexyl Dimethicone, Dilinoleamidopropyl Dimthylamine Dimethicone PEG-7 Phosphate, C26-28 Alkyl Dimethicone, PEG-8 Dimethicone, PPG-12 Dimethicone, Polysilicone-13, Trideceth-9 PG-Amodimethicone, Bis-PEG-12 Dimethicone Beeswax, Capric/Caprylic Triglyceride, Petrolatum, Mineral Oil, Lanolin Oil, *Cocos nucifera* (Coconut) Oil, *Olea Europea* (Olive) Fruit Oil, *Simmondsia Chinensis* (Jojoba) Seed Oil, *Prunus Armeniaca* (Apricot) Kernel Oil, *Crambe Abyssinica* Seed Oil, Vegetable Oil, *Zea Mays* (Corn) Oil, Acetylated Lanolin Alcohol, Cetearyl Isononanoate, Cetearyl Ethylhexanoate, Cetearyl Palmitate, Hydrogenated Olive Oil Hexyl Esters, Triethylhexanoin, Ceramide-3, Caprylyl Glycol, Cetyl Glycol, Glycerin, Panthenol, Phytantriol, Methanediol, Inositol, PPG-35-Buteth-45, PPG-5 Butyl Ether, Cocoamidopropyl Betaine, Coco-Betaine, Cocoamidopropyl Hydroxysultaine, Lauramidopropyl Betaine, Lauryl Betaine, Oleamidopropyl Betaine, Disodium Cocoamphodiacetate, Disodium Cocoamphodipropionate, Disodium Lauroamphodiacetate, Sodium Cocoamphopropionate, Sodium Cocoamphoacetate, Acetamide MEA, Behenamide MEA, Linoleamide DEA, Linoleamide MEA, Linoleamide MIPA, Linoleic Acid, Linolenic Acid, Maltodextrin, Niacin, Polyacrylate-1 Crosspolymer, Polyester-4, Pyridoxine HCl, Phytosphingosine, Salicylic Acid, Squalane, Squalene, Thiodiglycoamide, Zinc Pyrithione and mixtures thereof.

Non-limiting examples of proteins include collagen, deoxyribonuclease, iodized corn protein, milk protein, protease, serum protein, silk, sweet almond protein, wheat germ protein, wheat protein, alpha and beta helix of keratin proteins, hair proteins, such as intermediate filament proteins, high-sulfur proteins, ultrahigh-sulfur proteins, intermediate filament-associated proteins, high-tyrosine proteins, high-glycine tyrosine proteins, tricohyalin, and mixtures thereof.

Non-limiting examples of amino acids include amino acids derived from the hydrolysis of various proteins as well as the salts, esters, and acyl derivatives thereof. Non-limiting examples of such amino acid agents include amphoteric amino acids such as alkylamido alkylamines, i.e. stearyl acetyl glutamate, caprylol silk amino acid, caprylol collagen amino acids, caprylol keratin amino acids, caprylol pea amino acids, cocodimonium hydroxypropyl silk amino acids, corn gluten amino acids, cysteine, glutamic acid, glycine, hair keratin amino acids, amino acids such as asparatic acid, threonine, serine, glutamic acid, proline, glycine, alanine, cystine, valine, methionine, isoleucine, leucine, tyrosine, phenylalanine, cysteic acid, lysine, histidine, arginine, cysteine, tryptophan, citrulline, lysine, silk amino acids, wheat amino acids and mixtures thereof.

Non-limiting examples of cationic conditioners include quaternium-27, behenamidopropyl PG-dimonium chloride, hydroxyethyl tallowedimonium chloride, hexadimethrine chloride, stearalkonium chloride and cetrimonium chloride.

Non-limiting examples of cationic polymers include polyquaternium-4, polyquaternium-6, polyquaternium-7, polyquatemium-10, polyquatemium-11, polyquatemium-16, polyquatemium-22 and polyquaternium-32.

Non-limiting examples of nonionic surfactants includes alkoxylated derivatives of the following: fatty alcohols, alkyl phenols, fatty acids, fatty acid esters and fatty acid amides, wherein the alkyl chain is in the C12-50 range, typically in the C16-40 range, more typically in the C24 to C40 range, and having from about 1 to about 110 alkoxy groups. The alkoxy groups are selected from $C_2$-$C_6$ oxides and their mixtures, with ethylene oxide, propylene oxide, and their mixtures being the typical alkoxides. The alkyl chain may be linear, branched, saturated, or unsaturated. Of these alkoxylated non-ionic surfactants, the alkoxylated alcohols are typical, and the ethoxylated alcohols and propoxylated alcohols are more typical. The alkoxylated alcohols may be used alone or in mixtures with those alkoxylated materials disclosed herein-above.

Other representative examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10), steareth-10 (a stearyl alcohol ethoxylate having an average degree of ethoxylation of 10), steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and other derivatives and mixtures of the preceding.

Silicones include, but are not limited to, polyalkylsiloxane oils, linear polydimethylsiloxane oils containing trimethylsilyl or hydroxydimethylsiloxane end groups, polymethylphenylsiloxane, polydimethylphenylsiloxane or polydimethyldiphenylsiloxane oils, silicone resins, organofunctional siloxanes having in their general structure one or a number of organofunctional group(s), the same or different, attached directly to the siloxane chain or mixtures thereof. Organofunctional groups include, but are not limited to polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can be used either as a neat fluid or in the form of a pre-formed emulsion.

The conditioning agent can be present in an amount from about 0.001% to about 50% by weight of the composition. In another aspect, the conditioning agent can be present in an amount from about 0.1% to about 25% by weight of the composition. Still, in another aspect, the conditioning agent can be present in an amount from about 0.2% to about 10% by weight of the composition. Yet, in another aspect, the conditioning agent can be present in an amount from about 0.2% to about 2% by weight of the composition.

Chelants

The compositions for dyeing keratin fibers disclosed herein, including hair dyeing compositions, can comprise additional chelants. Suitable additional chelants are additional amino-phosphonic acid chelants. Amino-phosphonic acid chelants are defined as chelants comprising an amino-phosphonic acid moiety ($—PO_3H_2$) or its derivative $—PO_3R_2$, wherein $R^2$ is a $C_1$ to $C_6$ alkyl or aryl radical. Suitable aminophosphonic acid type and aminophosphonic acid type derivatives are described in U.S. Pat. No. 7,759,720, beginning at column 19, line 60, and ending at column 20, line 60, of which cited portion is incorporated herein by reference.

The hair dyeing compositions disclosed herein comprise from 0.01% to 5% by weight of amino-phosphonic acid type chelants, salts thereof, derivatives thereof and mixtures thereof. In another aspect, the amino-phosphonic acid type chelants, salts thereof, derivatives thereof and mixtures thereof are present in the hair dyeing compositions in an amount from 0.25% to 3% by weight of the composition. Still, in another aspect, the amino-phosphonic acid type chelants, salts thereof, derivatives thereof and mixtures thereof are present in the hair dyeing compositions in an amount from 0.25% to 1% by weight of the composition.

Other examples of chelants suitable for use herein include EDDS (ethylenediaminedisuccinic acid), and carboxylic acids (for example, aminocarboxylic acids). Chelants can be employed in the hair dyeing composition as stabilizers and/or preservatives. Additionally, chelants provide hair fiber damage benefits; and thus, they can be utilized to further improve the hair damage profile of the hair dyeing composition. Levels of chelants can be as low as about 0.1% by weight of the hair dyeing composition. In another aspect, chelants are present in an amount of at least about 0.25% by weight of the composition. Diamine-N,N'-dipolyacid and monoamine monoamide-N,N'-dipolyacid (for example EDDS) chelants are present in an amount of about 0.5% by weight of composition.

Solvents

The solvent is typically water, alcohol, glycol or mixtures thereof. Suitable solvents for use in the compositions of the present invention include, but are not limited to, water, ethanol, propanol, butanol, isopropylalcohol, benzyl alcohol, butoxydiglycol, 1,2 propane diol (propylene glycol), 1,3 propane diol, ethoxydiglycol, hexylene glycol, and dipropylene glycol, triethylene glycol, hexylene glycol, diethylene glycol, ethylene glycol, 1,3-butylene glycol (butylene glycol) and 1,2-butylene glycol. Solvents can be present in the keratin fiber dyeing composition in an amount between 30% to 95%, 35% to 90% or 40% to 75% by weight, based on the weight of the composition. Yet, in another aspect, concentrates of the keratin fiber dyeing composition can have one or more solvents present in an amount from 1% to 60%, 5% to 50% or 10% to 40% by weight, based on the weight of the composition.

Auxiliary Agents

Commercially available nonionic surfactants are BRIJ nonionic surfactants from Uniqema, Wilmington, Del. Typically, BRIJ is the condensation products of aliphatic alcohols with from about 1 to about 54 moles of ethylene oxide, the alkyl chain of the alcohol being typically a linear chain and having from about 8 to about 22 carbon atoms, for example, BRIJ 72 (i.e., Steareth-2) and BRIJ 76 (i.e., Steareth-10).

Nonionic surfactants include, but are not limited to, alkyl glycosides, which are the condensation products of long chain alcohols, e.g. C8-C30 alcohols, with sugar or starch polymers. These compounds can be represented by the formula (S)nOR, wherein S is a sugar moiety such as glucose, fructose, mannose, galactose, and the like; n is an integer of from about 1 to about 1000, and R is a C8-C30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Examples of these surfactants are alkyl polyglucosides wherein S is a glucose moiety, R is a C8-C20 alkyl group, and n is an integer of from about 1 to about 9. Also useful herein are sucrose ester surfactants such as sucrose cocoate and sucrose laurate.

Other nonionic surfactants suitable for use in the present invention are glyceryl esters and polyglyceryl esters, including but not limited to, glyceryl monoesters, typically glyceryl monoesters of C16-C22 saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of C16-C22 saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters, for example, sorbitan esters of C16-C22 saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate, sorbitan sesquioleate, sorbitan monoisostearate, sorbitan stearates, sorbitan trioleate, sorbitan tristearate, sorbitan dipalmitates, and sorbitan isostearate.

Also suitable for use as nonionic surfactants are alkoxylated derivatives of glyceryl esters, sorbitan esters, and alkyl polyglycosides, wherein the alkoxy groups is selected from the group consisting of C2-C6 oxides and their mixtures, with ethoxylated or propoxylated derivatives of these materials being typical. Non-limiting examples of commercially available ethoxylated materials include TWEEN (ethoxylated sorbitan mono-, di- and/or tri-esters of C12 to C18 fatty acids with an average degree of ethoxylation of from about 2 to 20).

Non-limiting examples of anionic surfactants include compounds in the classes known as alkyl sulfates, alkyl ether sulfates, alkyl sulfonates, alkyl ether sulfonates, sulfate esters of an alkylphenoxy polyoxyethylene ethanol, alpha-olefin sulfonates, beta alkyloxy alkene sulfonates, alkyl arylsulfonates, alkyl carbonates, alkyl ether carboxylates, fatty acids, succinamates, sulfosuccinates, sarcosinates, octoxynol or nonoxynol phosphates, taurates, fatty taurides, sulfated monoglycerides, fatty acid amino polyoxyethylene sulfates, isothienates and mixtures thereof. Specific examples of anionic surfactants include the ammonium, monoethanolamine, diethanolamine, triethanolamine, isopropylamine, sodium, potassium, lithium, or magnesium salts of lauryl sulfate, dodecylbenzene-sulfonate, lauryl sulfosuccinate, lauryl ether sulfate, lauryl ether carboxylate, lauryl sarcosinate, cocomethyl tauride, and sulfosuccinate half ester amide and mixtures thereof.

Non-limiting examples of amphoteric and zwitterionic surfactants include alkyl, alkyl dimethyl, alkylamido, alkyl amide, alkylamidopropyl, or alkyl dimethylammonium betaine; alkyl amidopropyl or alkyl sulfobetaine; alkyl, alkylampho, or alkylamphocarboxy glycinate; alkyl, or alkyl substituted imidazoline mono or dicarboxylate; sodium salts of alkyl mono- or dicarboxylates; alkyl beta amino acids; alkyl amidopropyl, or alkyl ether hydroxysultaine; alkyl amidopropyl dimethyl ammonia acetate; alkyl ampho mono- or diacetate; alkyl, or alkyl ampho, or alkyl imino dipropionate; alkyl amphopropionate; alkyl beta amino propionic acid; alkyl dipropionate; alkyl beta iminodipropionate; branched or n-alkyl dimethylamidopropionate; alkyl carboxylated propionate; alkyl, or methyl alkyl imidazoline; fluorinated alkyl amphoteric mixtures; and/or nonionic surfactants such as, but not limited to, alkyl, alkyl dimethyl, alkyl amidopropylamine, or bis 2-hydroxy ethyl alkyl amine oxides; alkanolamides; alkyl amides; polyoxyethylene glycol (PEG) of monoglycerides, of sorbitan esters, of branched or linear fatty alcohol ethers, of branched or linear fatty acid ethers, of thioethers; alkyl oxoalcohol PEG; PEG fatty esters; polyoxyethlyene glycol/polyoxpropylene glycol block copolymers; alkyl phenol PEG ethers; alkyl polyglucosides, or polysaccharides, polysiloxane polyethoxylene ether and mixtures thereof.

Specific examples include cocamidopropyl betaine, lauramidopropyl betaine, coco/oleamidopropyl betaine, lauryl betaine, coco betaine, oleyl betaine, cocamidopropyl hydroxysultaine, tallowamidopropyl hydroxysultaine, dihydroxyethyl tallow glycinate, disodium cocoamphodiacetate, disodium cocoamphodipropionate and mixtures thereof.

Anti-dandruff agents such as zinc pyrithione, salicylic acid, climbazole, ketoconazole, sulfur piroctone olamine, selenium sulfide and mixtures thereof may also be used as an auxiliary ingredient.

Finally, hair dyeing compositions according to the present invention can be provided in any usual form, such as for example an aqueous composition, a powder, a gel, an oil-in-water emulsion, a wax or a concentrate.

Method of Use

It is understood that the methods of use described herein are for illustrative purposes only and that various modifications or changes in light thereof will be suggested to one of ordinary skill in the art without departing from the scope of the present invention.

Hair dye compositions are usually sold in kits comprising an individually packaged dye component (also called "dye cream" for emulsions or "dye liquid" for solutions) comprising the dye precursors and alkalizing agent in a suitable carrier, and an individually packaged hydrogen peroxide component (also called "hydrogen peroxide cream" for emulsions or "hydrogen peroxide liquid" for solutions) comprising the oxidizing agent. The consumer or hair technician mixes the dye component and hydrogen peroxide component together immediately before use and applies it onto the hair.

The aminophosphonic acid type chelants of the present invention can be comprised within the dye component or the hydrogen peroxide component or both. If present, the additional chelant(s) such as EDDS, can also be present in the dye component and or the hydrogen peroxide component. Typically, the additional chelants are provided in the tint.

After working the mixture for a few minutes (to ensure uniform application to all of the hair), the dye or bleaching composition is allowed to remain on the hair for an amount sufficient for the dyeing to take place (usually about 2 to 60 minutes, but can be from about 30 to 45 minutes). The hair is then thoroughly rinsed with water and allowed it to dry. It will be observed that the hair has changed from its original color to the desired color.

When present in the dye composition, the optional conditioning agent can be provided in a third container. In the latter case, all three compositions can be mixed immediately before use and applied together, or the content of the third container can be applied (after an optional rinse step) as a post-treatment immediately after the oxidative dye composition resulting from the mixture of the other containers.

The compositions disclosed herein can be utilized in a variety of packaging and dispensing devices. These dispensing devices can come in the form of separate devices which may be used independently or in combination with one another. Typically, the hair coloring or bleaching compositions are contained within separate single or multi compartment containers so that the compositions can be stored separately from one another before use. The compositions are then mixed together by a mixing means and then applied to the consumer's hair by an application means. The dye system can also be part of a dye rinse or shampoo.

The most common packaging device which can be used for the present invention involves storing the developer in a container such as a bottle, tube, aerosol, or a sachet and separately storing the dye lotion in an additional compartment within the developer container or in a separate container which may be identical such as a dual sachet or aerosol system, for example or different such as a bottle and tube system.

The consumer can mix the developer lotion and the dye lotion by any means. This can involve the use of a mixing bowl into which the lotions are dispensed and then mixed. Alternatively, it can involve the addition of one of the lotions into the container of the other lotion, (typically the dye lotion is added to the developer lotion), followed by manual shaking or mixing. Another system involves the perforation or displacement of a seal located between the separate compartments of the dye and developer lotion within a single container or sachet followed by manual mixing within the container or in a separate and or additional container.

The following examples reflect hair dye compositions and uses thereof and are not meant to be limiting.

EXAMPLES

Example 1

This is a prophetic example that is intended to demonstrate the composition of a temporary hair dye and a method of manufacturing of a temporary hair dye. Temporary dye compositions are based on hair and textile dyes having molecules that are too large to penetrate the fiber shaft. The color rinses out after a single shampoo application to the hair. Temporary dyes are also called direct dyes. Temporary dyes add color to hair but they cannot lighten hair color. Table 1 below details compositions of temporary hair dyes. All weights in the Table 1 are given in grams.

TABLE 1

| Ingredient | weight in grams |
|---|---|
| Part A | |
| DI water | 34.55 |
| Carbopol Aqua SF-1 (acrylates copolymer, 30%)[1] | 10 |
| Part B | |
| DI water | 15 |
| disodium EDTA | 0.05 |
| Ketal* | 5 |
| Miranol Ultra-C37 (sodium cocoamphoacetate (37%))[2] | 15 |
| cocamidopropyl betaine (15%) | 3 |
| Polyquaternium-39 | 0.8 |
| Part C | |
| Germaben II (propylene glycol (and diazolidinyl urea (and) methylparaben (and) propylparaben)[3] | 0.45 |
| sodium hydroxide (18%) | 0.25, adjust to pH 7 |
| Part D | |
| DI water | 8 |
| Arianor Sienna Brown (Basic brown 27/CI 12251)[4] | 0.25 |
| Arianor Steel Blue (Basic blue 99/CI 56059)[4] | 0.125 |
| Arianor Madder Red (basic red 76/CI 12245)[4] | 0.125 |
| Dow Corning 193 (PEG-12 dimethicone)[5] | 0.2 |
| Part E | |
| decyl glucoside (50%) | 4 |
| DI water | 3 |
| Timiron MP-149 Diamond Cluster (mica and titanium dioxide)[6] | 0.2 |

[1]from Lubrizol/Noveon Consumer Specialties;
[2]from Rhodia;
[3]from ISP;
[4]from Warner Jenkinson;
[5]from Dow Corning;
[6]from Rona;
*example A: ketal is Et-LGK; Example B: ketal is methyl-LGK. Example C: ketal is methyl-LPK.

The method for manufacturing the compositions in the Table 1 is as follows:

Slowly add Carbopol to DI (deionized) water (Part A). In a separate vessel, dissolve EDTA in DI water at approximately 50° C. and then add the remaining ingredients of Part B individually with mixing. Part B is slowly added to Part A with moderate mixing. Add the ingredients of Part C individually to the combined Parts A/B to form a main batch, which comprises Part A, Part B and Part C, adjusting the amount of sodium hydroxide so that the pH of the batch is 7. In a separate vessel, dissolve dyes in DI water, keeping temperature below 60° C., and then add PEG-12 dimethicone.

Add Part D to main batch, which now comprises Part A, Part B, Part C and Part D. In a separate vessel, prepare Part E by dispersing the pigments in the other ingredients of Part E. Add Part E to the main batch to form the temporary hair dye.

Example 2

This is a prophetic example intended to demonstrate the composition of a semi-permanent hair dye composition and the manufacturing of a semi-permanent hair dye composition. Just like temporary dyes, these formulations rely on direct dyes. However, the semi-permanent dyes comprise smaller molecules based on nitro-phenylene-diamine and due to their small size, the direct dyes in the semi-permanent formulations can penetrate the fiber shaft. As a result, semi-permanent hair dyes can survive about 6 to about 8 shampoo applications to the hair. Table 2 below details compositions of temporary hair dyes. All weights in the Table 2 are given in grams.

TABLE 2

| Ingredient | Weight in grams |
|---|---|
| Part A | |
| DI water | 64 |
| Carbomer | 0.5 |
| CROSULTAINE-C50[2] (Cocamidopropyl hydroxysultaine) | 7 |
| BRIJ O20 (Oleth-20)[2] | 0.4 |
| triethanolamine | 0.4 |
| Part B1 (for light/medium brown) | |
| DI water | 11.5 |
| HC Blue #2 CP[1] | 1.5 |
| HC Red #1[1] | 0.6 |
| HC Yellow #4[1] | 0.5 |
| Part B2 (for dark brown/black) | |
| DI water | 10.6 |
| HC Blue #2 CP[1] | 2.5 |
| HC Red #1[1] | 0.4 |
| HC Yellow #4[1] | 0.6 |
| Part B3 (for auburn) | |
| DI water | 12.1 |
| HC Blue #2 CP[1] | 0.3 |
| HC Red #1[1] | 1.5 |
| HC Yellow #4[1] | 0.2 |
| Part C | |
| SD alcohol 40 | 3 |
| Ketal* | 3 |
| CROTHIX LIQUID[2] (PET-150 pentaerythrityl tetrastearate (and) PEG-6 caprylic/capric glycerides (and) water | 3 |
| Crodasone W[2] (Hydrolyzed Wheat Protein PG-propyl silanetriol) | 3 |
| Germaben II[3] (propylene glycol (and) diazolidinyl urea (and) methylparaben (and) propylparaben) | 1 |

[1]from Jos. H. Lowenstein and Sons;
[2]from Croda;
[3]from ISP;
*example A: ketal is Et-LGK; example B: ketal is Et-LPK. Example C: ketal is methyl-LGK. Example D: ketal is methyl-LPK. Example E: ketal is propyl-LGK The process to manufacture the composition of Table 2 is as follows. Carbomer is disposed into water slowly while rapidly mixing the solution and heating the mixture to 65° C. When uniformly dispersed, add remaining ingredients of Part A one at a time, while mixing at moderate speed. Combine ingredients of Part B (either Part B1, Part B2 or Part B3) with mixing while heating to a temperature to 65° C. Add part B to Part A, mixing well. Continue mixing and cool to 40° C. Add ingredients of Part C individually to the mixture of Part A and Part B, mixing well after each addition.

Example 3

This is a prophetic example intended to demonstrate the composition for a semi-permanent hair dye gel composition having a dark brown color. This example also details a method of manufacturing the composition in the Table 3.

TABLE 3

| Ingredient | Weight in grams |
|---|---|
| Part A | |
| H.C. Blue #2 solid | 0.36 |
| Lowadene Violet #1[1] | 0.56 |
| H.C. Yellow #4 | 0.24 |
| Lowadene Blue 61505[1] | 0.2 |
| Lowadene Blue 62500[1] | 0.17 |
| H.C. Yellow #5 | 0.02 |
| Ketal* | 6 |
| DI water | 18.34 |
| Part B | |
| oleic acid | 0.82 |
| ethanolamine | 0.18 |
| Part C | |
| Monamid ISO-ADY (linoleamide DEA)[2] | 2 |
| Part D | |
| Structure 2001 polymer (acrylates/steareth-20 itaconate copolymer)[3] | 3.39 |
| DI water | 60.11 |
| Part E | |
| ethanol amine | 2.5 |
| Part F | |
| citric acid (10%) | 5 |

[1]Jos. H. Lowenstein & Sons, Inc;
[2]Uniqema/Croda;
[3]AkzoNobel;
*example A: ketal is Et-LGK; Example B: ketal is methyl-LGK. Example C: ketal is methyl-LPK. Example D: ketal is propyl-LGK The composition is manufactured as follows. With moderate overhead agitation, heat Part A to about 50 to about 60° C. and mix dyes well. Cool to 40° C. Add Part B and Part C to Part A and mix well. Add Part D to the dye solution and mix well. Add Part E to the dye solution and mix well. Finally, add Part F to dye solution and mix well.

Example 4

This is a prophetic example intended to demonstrate a composition used to manufacture a permanent hair dye composition. A method of manufacturing the permanent hair dye is also described. Permanent hair dyes are based on oxidative dye chemistry and are formulated in two packages that are mixed at the time of dyeing. One package contains color dye intermediates in an alkaline solution, while the other package contains the peroxide activator that both lightens hair and converts the dye intermediate to its color form. Because permanent hair dye formulations can dye as well as bleach hair, hair can be dyed to a lighter shade than its natural color. Table 4 demonstrates the composition of a permanent hair dye.

TABLE 4

| Ingredients | Weight in grams |
|---|---|
| Phase A | |
| Deionized Water | 52.51 |
| Sodium sulfite | 0.30 |
| EDTA | 0.20 |
| Erythorbic acid | 0.30 |
| p-Phenylenediamine | 1.70 |
| 4-amino-2-hydroxytoluene | 0.06 |
| Resorcinol | 1.40 |
| o-Aminophenol | 1.40 |
| Toluene-2, 5-diamine Sulfate | 0.11 |
| 1-Napthol | 0.02 |
| Ketal* | 3 |
| Incromide CA (Cocamide DEA) | 3.50 |
| Incromectant AMEA-100 (Acetamide MEA) | 1.00 |
| Phase B | |
| KeraTint EZ ((Cetyl alcohol [and] stearyl alcohol [and] PPG-5 ceteth-20 & Dicetyl Phosphate [and] ceteth-10 phosphate [and] behentrimonium methosulfate) | 12 |
| Ketal* | 9 |
| Phase C | |
| Crodasone W (hydrolyzed wheat protein PG-propyl silanetriol) | 2.00 |
| Crosilkquat (Cocamidopropyl hydroxypropyl silk amino acids) | 0.50 |
| Crosultaine C-50 (Cocamidopropyl hydroxysultaine) | 1.00 |
| Phase D | |
| Ammonia | 10.00 |

*example A: ketal is Et-LGK; example B: ketal is Et-LPK. Example C: ketal is methyl-LGK. Example D: ketal is methyl-LPK. Example E: ketal is propyl-LGK. Example F: at least one of the ketals is Et-LPK.

The method of manufacturing of the composition of Table 4 is as follows.

Combine the ingredients of phase A in a main vessel and heat to 75° C. In a separate vessel, heat phase B to 75° C. Add phase B to phase A with mixing. Cool to 50° C. and add ingredients of phase C individually, mixing well after each addition. Cool to 40° C., add phase D and mix until homogenous. This formulation must be mixed with a hydrogen peroxide developer prior to use.

Examples 5 and 6

Hair dye formulations were prepared from the ingredients in Table 5.

TABLE 5

| Ingredient (wt.%) | 5A | 5B | 6A | 6B |
|---|---|---|---|---|
| Water | 60.19 | 60.19 | 60.19 | 60.19 |
| Alkyl polyglucoside | 1.76 | 1.76 | 1.76 | 1.76 |
| Oleic acid | 14.00 | 14.00 | 14.00 | 14.00 |
| Nonoxynol-1 | 3.70 | 3.70 | 3.70 | 3.70 |
| Nonoxynol-4 | 5.00 | 5.00 | 5.00 | 5.00 |
| EDTA (4Na) | 0.05 | 0.05 | 0.05 | 0.05 |
| Et-LGK | 7.00 | 7.00 | 0 | 0 |
| Et-LPK | 0 | 0 | 7.00 | 7.00 |
| Isopropanol 99% | 7.00 | 7.00 | 7.00 | 7.00 |
| Ammonium hydroxide | 0.80 | 0.80 | 2.10 | 2.10 |
| Erythorbic acid | 0.40 | 0.40 | 0.40 | 0.40 |
| Sodium sulfite | 0.10 | 0.10 | 0.10 | 0.10 |
| qs. to pH | | | | |
| Final pH | 10.2 | 8.5 | 10.2 | 8.5 |

Saturated solutions of each oxidation dye intermediate were prepared in Examples 5A and 6A at pH 10.2, and Examples 5B and 6B at pH 8.5. Three replications were prepared for each example. The saturated solutions were prepared by equilibrating three 50 g samples of each of the variations at 27° C. in a water bath. Once the bases were at the desired temperature, excessive amounts (i.e., more than would dissolve) of p-phenylenediamine, 1-naphthol and p-toluenedaimine sulfate were added to portions of each base pH combinations. The resultant mixtures were maintained at 27° C. for 10 minutes with stirring to dissolve the maximum possible amount of each intermediate under these conditions.

At the end of the 10 minutes the samples were withdrawn from the water bath and pipetted to 500 ppm in Solvent A then scanned in a UV-Vis spectrophotometer and compared to a calibration curve of known dye concentration in a standard solvent (Solvent A, below) to determine concentration.

A calibration curve for dye concentration was prepared by preparing 1.0% (w/w) solutions of the oxidation dye intermediates: p-phenylenediamine (PPD), 1-naphthol and p-toluenediamine sulfate (PTD) were prepared in Solvent A (0.2% EDTA, 0.4% erythorbic acid, 0.4% sodium sulfite, 49.5% DI water (RO filtered), and 49.5% isopropanol). The solutions were diluted stepwise from 1.00% to 0.00001% (10 ppm) and scanned with a Varian DSM 200 from a range of 380 nm to 900 nm. Absorption maxima in the visible range were used to plot concentration curves with an optimal absorbance for viewing at approximately 500 ppm. Results are shown in Table 6.

TABLE 6

| | Ingredient | 5A | 5B | 6A | 6B |
|---|---|---|---|---|---|
| Average Solubility % wt./wt. | p-phenylenediamine | 0.07 | 0.07 | 0 | <0.01 |
| | 1-naphthol | 0.14 | 0.08 | 0.01 | <0.01 |
| | p-toluenediamine sulfate | 0.35 | 0 | 0.01 | 0 |
| Visual | | Clear | Clear | Trapped bubbles | Clear |

All formulations resulted in viscosities of less than 150 cP on a Brookfield RVT. All formulations were initially clear, except formulation 6A, which had trapped bubbles that produced a cloudy, yet translucent, formulation.

Example 7

This example demonstrates the use of various moieties in hair dyes. The moieties are p-phenylene diamine, p-toluenediamine sulfate, resorcinol and m-aminophenol. The respective hair dye compositions and their methods of manufacturing are discussed in detail below.

p-Phenylene Diamine p-Phenylene diamine (97% purity, available from Alfa Aesar) was dissolved at 5% solids in the glycerol ketal of ethyl levulinate (Et-LGK) at 80° C. and formed a very dark solution with no evidence of precipitation. The active was still soluble after 24 hours of storage at room temperature.

p-Phenylene diamine partially dissolved at 25% solids in the butyl ketal of ethyl levulinate (Bu-LGK) at 80° C. and formed a dark solution with precipitant on the bottom. p-phenylene diamine was dissolved at 5% solids in Bu-LGK at 80° C. and formed a very dark solution with no evidence of precipitation.

p-Phenylene diamine did not completely dissolve at 5% solids in Et-LPK 80° C. An orange solution with precipitant formed. P-phenylene diamine did not completely dissolve at 1% solids in propyl glycol ketal of ethyl levulinate (Et-LPK) 80° C. An orange solution with precipitant formed. In both cases, the solution turned darker orange with time during storage at room temperature but a precipitant remained.

p-Toluenediamine Sulfate p-Toluenediamine sulfate (97% purity, available from Aldrich) partially dissolved at 1% solids in Et-LGK at 80° C. The sample formed a brown solution with solid precipitant on the bottom. p-Toluenediamine sulfate partially dissolved at 0.1% solids in Et-LGK at 80° C. The sample formed a brown solution with solid precipitant on the bottom.

p-Toluenediamine sulfate failed to dissolve at both 1% solids and 0.1% solids in Et-LPK at 80° C. The sample formed milky white mixture with solids at the bottom of the vial. No color development occurred.

Resorcinol

Resorcinol (at 99% purity available from Alfa Aesar) was dissolved at 10% solids in Et-LGK at 80° C. with agitation. The mixture was still soluble after 24 hours of storage at room temperature.

Resorcinol was dissolved at 10% solids in Bu-LGK at 80° C. with agitation. The mixture was still soluble after 24 hours of storage at room temperature.

Resorcinol was dissolved at 10% solids in Et-LPK at room temperature with agitation. The mixture was still soluble after 24 hours of storage at room temperature.

m-Aminophenol m-Aminophenol was dissolved at 5% solids in Et-LGK at room temperature. The mixture was still soluble after 24 hours of storage at room temperature.

m-Aminophenol was dissolved at 5% solids in Et-LPK at 80° C. with agitation. The mixture was still soluble after 24 hours of storage at room temperature.

The aforementioned examples provide a variety of different compositions in which the dyes and other ingredients can be used in different amounts in order to provide different types of dyes. The following Table 7 lists nested ranges for the various ingredients that may be used in temporary, permanent, semi-permanent and demi-permanent hair dyes.

TABLE 7

| Oxidative Dyes | |
|---|---|
| Oxidation base | 0.0005% to 25% |
| | 0.005% to 20% |
| | 0.05% to 15% |
| | 0.05% to 10% |
| Coupler | 0.0001% to 25% |
| | 0.0001% to 20% |
| | 0.001% to 10% |
| | 0.05% to 8% |
| Reducer | 0.01% to 8% |
| | 0.05 to 3% |
| Oxidative dye precursor | 0.0005% to 25% |
| | 0.005% to 20% |
| | 0.01% to 15% |
| | 0.01% to 10% |
| | 0.05% to 5% |

| Direct Dyes | |
|---|---|
| direct dye | 0.001% to 20% |
| | 0.001% to 10% |
| | 0.001% to 8% |
| | 0.005% to 5% |
| | 0.01% to 2.5% |
| | 0.01% to 2% |
| | 0.01% to 1% |

| Surfactants | |
|---|---|
| Surfactants | 0.001% to 50% |
| | 0.001% to 30% |

TABLE 7-continued

| | 0.01% to 20% |
|---|---|
| | 0.05% to 15% |
| | 0.05% to 10% |

| Pigments | |
|---|---|
| | 0.01% to 60% |
| | 0.01% to 30% |
| | 0.01% to 20% |
| | 0.01% to 10% |

| Liposoluble | |
|---|---|
| Liposoluble dye | Up to 30% |
| | Up to 10% |
| | Up to 6% |

| Solvents | |
|---|---|
| Ketal and solvent | 30% to 95% |
| | 35% to 90% |
| | 40% to 75% |
| | 1% to 60% |
| | 5% to 50% |
| | 10% to 40% |

All cited patents, patent applications, and other references are incorporated herein by reference in their entirety.

The various embodiments described above are provided by way of illustration only and should not be construed to limit the claims attached hereto. The present invention can suitably comprise, consist of, or consist essentially of, any of the disclosed or recited elements. Thus, the invention illustratively disclosed herein can be suitably practiced in the absence of any element, which is not specifically disclosed herein. Various modifications and changes will be recognized that can be made without following the example embodiments and applications illustrated and described herein, and without departing from the true spirit and scope of the following claims.

What is claimed is:

1. A keratin fiber dyeing composition comprising:
   at least one colorant,
   at least one solvent, and
   a ketal adduct of formula (I)

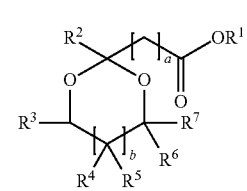

wherein
   $R^1$ is $C_{1-6}$ alkyl,
   $R^2$ is hydrogen or $C_{1-3}$ alkyl,
   each $R^3$, $R^4$, and $R^5$ is independently hydrogen or $C_{1-6}$ alkyl,
   $R^6$ is hydrogen or $C_{1-6}$ alkyl, or hydroxymethyl,
   $R^7$ is hydrogen, $C_{1-6}$ alkyl, $C_{1-6}$ alkyl substituted with up to four $OR^8$ groups wherein $R^8$ is hydrogen, $C_{1-6}$ alkyl, or acetyl,
   a is 0-3, and
   b is 0-1.

2. The composition of claim 1, wherein $R^1$ is $C_{1-6}$ straight chain or branched alkyl, $R^2$ is methyl, each $R^3$, $R^4$, and $R^5$ is independently hydrogen or $C_{1-3}$ alkyl, $R^6$ is hydrogen, $C_{1-3}$ alkyl, or hydroxymethyl, $R^7$ is hydrogen, $C_{1-3}$ alkyl, or $C_{1-4}$ alkyl substituted with up to four —$OR^8$ groups wherein $R^8$ is hydrogen or a $C_{1-3}$ alkyl group, a is 1-3, and b is 0-1.

3. The composition of claim 1, wherein each $R^1$ and $R^4$ is independently $C_{1-6}$ straight chain or branched alkyl, each $R^2$ and $R^3$ is independently hydrogen or $C_{1-3}$ alkyl, each $R^6$, $R^7$, $R^{10}$, and $R^{11}$ is independently hydrogen, $C_{1-4}$ alkyl, $C_{1-6}$ hydroxyalkylene, or $C_{1-6}$ alkyl substituted with up to four hydroxy groups, each $R^8$ and $R^9$ is independently hydrogen, hydroxyl, $C_{1-4}$ alkyl, or $C_{1-4}$ hydroxyalkyl, a is 1-3, and b is 0-1.

4. The composition of claim 1, wherein $R^1$ is $C_{1-4}$ alkyl, $R^2$ is methyl, $R^3$ is hydrogen, $R^6$ is hydrogen, $C_{1-3}$ alkyl, or hydroxymethyl, $R^7$ is hydrogen, $C_{1-3}$ alkyl, or $C_{1-4}$ alkyl substituted with up to four —OR' groups wherein $R^8$ is hydrogen or a $C_{1-3}$ alkyl group, a is 2-3, and b is 0.

5. The composition of claim 1, wherein $R^1$ is $C_{1-4}$ alkyl or acetyl, $R^2$ is methyl, $R^3$ is hydrogen, $R^6$ is hydrogen, methyl, ethyl, or —$CH_2OH$, $R^7$ is methyl, ethyl, —$CH_2OH$, —$CH_2OCH_3$, —$CH_2OCH_2CH_3$, —$CH(OH)CH_2OH$, or —$(CH(OH))_3CH_2OH$, a is 2, and b is 0.

6. The composition of claim 1, wherein the ketal adduct is of formula (1a):

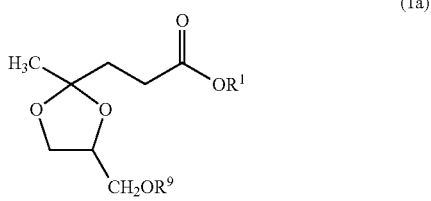

(1a)

wherein $R^1$ is a $C_{1-4}$ alkyl, and $R^9$ is hydrogen or $C_{1-4}$ alkyl.

7. The composition of claim 1, wherein the ketal adduct is of formula (1b)

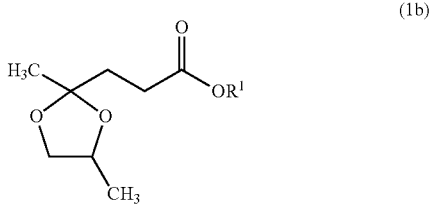

(1b)

wherein $R^1$ is a $C_{1-4}$ alkyl.

8. The composition of claim 1, wherein the solvent is water, alcohol, glycol, or mixtures thereof.

9. The composition of claim 1, wherein the solvent is water, ethanol, propanol, butanol, isopropylalcohol, benzyl alcohol, butoxydiglycol, 1,2 propane diol, 1,3 propane diol, ethoxydiglycol, hexylene glycol, and dipropylene glycol, triethylene glycol, hexylene glycol, diethylene glycol, ethylene glycol, 1,3-butylene glycol, or 1,2-butylene glycol.

10. The composition of claim 1, further comprising a cosolvent.

11. The composition of claim 10, wherein the cosolvent is different from the solvent and is water, ethanol, propanol, butanol, isopropylalcohol, benzyl alcohol, butoxydiglycol, 1,2 propane diol, 1,3 propane diol, ethoxydiglycol, hexylene glycol, and dipropylene glycol, triethylene glycol, hexylene glycol, diethylene glycol, ethylene glycol, propylene glycol, 1,3-butylene glycol, or 1,2-butylene glycol.

12. The composition of claim 1, further comprising at least one component selected from at least one oxidizing agent, at least one carbonate ion source, at least one alkalizing agent, at least one pH buffer, at least one radical scavenger, at least one surfactant, at least one gel network thickener, at least one polymer, at least one conditioning agent, at least one chelant, or at least one auxiliary agent.

13. The composition of claim 12, wherein the at least one auxiliary agent is an amino acid, a protein, a cationic conditioner, a cationic polymer, a wax, an antioxidant, a vitamin, an alpha hydroxy acid, a beta hydroxy acid, an alpha ketoacid, an antibacterial agent, a preservative, a perfume, a sequestering agent, an anti-dandruff agent, a botanical extract, a skin protectant, or mixtures thereof.

14. A keratin fiber dyeing composition comprising:
at least one hair colorant and
a ketal adduct of formula (1)

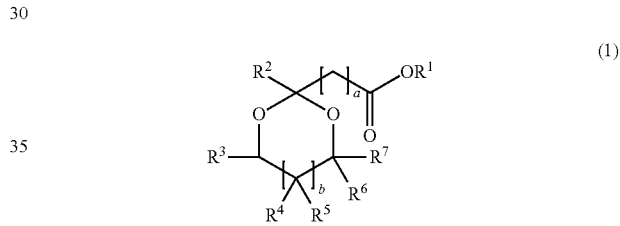

(1)

wherein
$R^1$ is $C_{1-6}$ straight chain or branched alkyl,
$R^2$ is hydrogen or $C_{1-3}$ alkyl,
each $R^3$, $R^4$, and $R^5$ is independently hydrogen or $C_{1-6}$ straight chain or branched alkyl,
$R^6$ is hydrogen or $C_{1-6}$ straight chain or branched alkyl, or hydroxymethyl,
$R^7$ is hydrogen, $C_{1-6}$ straight chain or branched alkyl, $C_{1-6}$ alkyl substituted with up to four $OR^8$ groups wherein $R^8$ is hydrogen, $C_{1-6}$ straight chain or branched alkyl, or acetyl,
a is 0-3, and
b is 0-1.

15. The composition of claim 14, wherein $R^1$ is $C_{1-6}$ alkyl, $R^2$ is methyl, each $R^3$, $R^4$, and $R^5$ is independently hydrogen or $C_{1-3}$ alkyl $R^6$ is hydrogen, $C_{1-3}$ alkyl, or hydroxymethyl, $R^7$ is hydrogen, $C_{1-3}$ alkyl, or $C_{1-4}$ alkyl substituted with up to four —$OR^8$ groups wherein $R^8$ is hydrogen or a $C_{1-3}$ alkyl group, a is 1-3, and b is 0-1.

16. The composition of claim 14, wherein each $R^1$ and $R^4$ is independently $C_{1-6}$ alkyl, each $R^2$ and $R^3$ is independently hydrogen or $C_{1-3}$ alkyl, each $R^6$, $R^7$, $R^{10}$, and $R^{11}$ is independently hydrogen, $C_{1-4}$ alkyl, $C_{1-6}$ hydroxyalkylene, or $C_{1-6}$ alkyl substituted with up to four hydroxy groups, each $R^8$ and $R^9$ is independently hydrogen, hydroxyl, $C_{1-4}$ alkyl, or $C_{1-4}$ hydroxyalkyl, a is 1-3, and b is 0-1.

17. The composition of claim 14, wherein $R^1$ is $C_{1-4}$ alkyl, $R^2$ is methyl, $R^3$ is hydrogen, $R^6$ is hydrogen, $C_{1-3}$ alkyl, or hydroxymethyl, $R^7$ is hydrogen, $C_{1-3}$ alkyl, or $C_{1-4}$ alkyl substituted with up to four —OR' groups wherein $R^8$ is hydrogen or a $C_{1-3}$ alkyl group, a is 2-3, and b is 0.

18. The composition of claim 14, wherein $R^1$ is $C_{1-4}$ alkyl or acetyl, $R^2$ is methyl, $R^3$ is hydrogen, $R^6$ is hydrogen, methyl, ethyl, or —$CH_2OH$, $R^7$ is methyl, ethyl, —$CH_2OH$, —$CH_2OCH_3$, —$CH_2OCH_2CH_3$, —$CH(OH)CH_2OH$, or —$(CH(OH))_3CH_2OH$, a is 2, and b is 0.

19. The composition of claim 14, wherein the ketal adduct is of formula (1a):

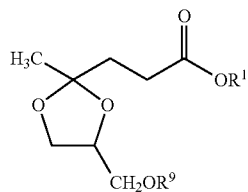

(1a)

wherein $R^1$ is a $C_{1-4}$ alkyl, and $R^9$ is hydrogen or $C_{1-4}$ alkyl.

20. The composition of claim 14, wherein the ketal adduct is of formula (1b)

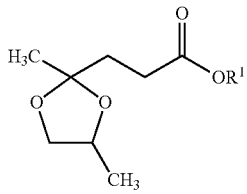

(1b)

wherein $R^1$ is a $C_{1-4}$ alkyl.

21. The composition of claim 14, further comprising at least one component selected from at least one oxidizing agent, at least one carbonate ion source, at least one alkalizing agent, at least one pH buffer, at least one radical scavenger, at least one surfactant, at least one gel network thickener, at least one polymer, at least one conditioning agent, at least one chelant, or at least one auxiliary agent.

22. The composition of claim 21, wherein the at least one auxiliary agent is an amino acid, a protein, a cationic conditioner, a cationic polymer, a wax, an antioxidant, a vitamin, an alpha hydroxy acid, a beta hydroxy acid, an alpha ketoacid, an antibacterial agent, a preservative, a perfume, a sequestering agent, an anti-dandruff agent, or mixtures thereof.

* * * * *